(12) United States Patent
Izumi et al.

(10) Patent No.: US 7,048,876 B2
(45) Date of Patent: May 23, 2006

(54) CHROMENE COMPOUND

(75) Inventors: Shinobu Izumi, Tokuyama (JP); Hironobu Nagoh, Tokuyama (JP)

(73) Assignee: Tokuyama Corporation, Yamaguchi (JP)

( * ) Notice: Subject to any disclaimer, the term of this patent is extended or adjusted under 35 U.S.C. 154(b) by 345 days.

(21) Appl. No.: 10/311,205

(22) PCT Filed: May 1, 2002

(86) PCT No.: PCT/JP02/04362

§ 371 (c)(1),
(2), (4) Date: Apr. 11, 2003

(87) PCT Pub. No.: WO02/090342

PCT Pub. Date: Nov. 14, 2002

(65) Prior Publication Data

US 2004/0094753 A1    May 20, 2004

(30) Foreign Application Priority Data

May 2, 2001  (JP) .............................. 2001-135074
Aug. 8, 2001 (JP) .............................. 2001-240712

(51) Int. Cl.
*C02B 5/23*   (2006.01)
*C07D 311/78*  (2006.01)
*C07D 311/94*  (2006.01)
*G03C 1/685*   (2006.01)

(52) U.S. Cl. .................... 252/586; 549/381; 430/270.1
(58) Field of Classification Search ................ 252/586
See application file for complete search history.

(56) References Cited

U.S. PATENT DOCUMENTS

| | | | |
|---|---|---|---|
| 5,645,767 A * | 7/1997 | Van Gemert ................ | 252/586 |
| 6,113,814 A * | 9/2000 | Gemert et al. ............... | 252/586 |
| 6,197,225 B1 * | 3/2001 | Tanizawa et al. ............ | 252/586 |
| 6,362,248 B1 * | 3/2002 | Hara et al. .................... | 522/26 |
| 6,506,538 B1 * | 1/2003 | Breyne et al. ......... | 430/270.17 |
| 6,558,583 B1 * | 5/2003 | Breyne et al. .............. | 252/586 |
| 2001/0025948 A1 * | 10/2001 | Walters et al. .............. | 252/586 |

FOREIGN PATENT DOCUMENTS

| | | | |
|---|---|---|---|
| CA | 2343310 | * | 9/1999 |
| JP | 2000344762 | * | 12/2000 |
| WO | WO 00/15629 | * | 9/1999 |
| WO | WO 00/15628 | * | 3/2000 |
| WO | WO 02/30916 | * | 4/2002 |

* cited by examiner

*Primary Examiner*—Randy Gulakowski
*Assistant Examiner*—Timothy J. Kugel
(74) *Attorney, Agent, or Firm*—Sherman & Associates

(57) ABSTRACT

A chromene compound typically represented by the following formula,

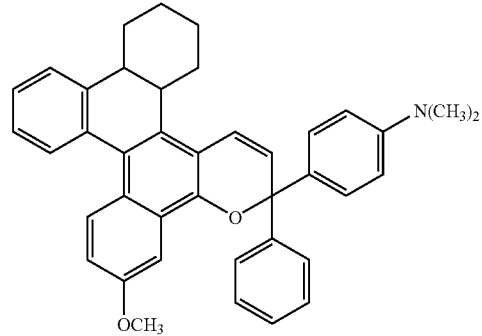

When placed in a state of developing color, the chromene compound exhibits absorption bands in two wavelength regions of 440 to 500 nm and 570 to 630 nm. A difference in the absorption intensity between the two absorption bands is small, and an intensity ratio in the color density in the two absorption bands is usually in a range of from 0.7 to 1.2. A color tone of a neutral tint such as grey or brown is obtained by using a single compound.

15 Claims, 2 Drawing Sheets

CHROMENE COMPOUND

TECHNICAL FIELD

The present invention relates to a novel chromene compound and to the use of the chromene compound.

BACKGROUND ART

Photochromism is a phenomenon that is drawing attention in these several years, and is a reversible action of a compound which quickly changes its color (called development of color) when it is irradiated with light containing ultraviolet rays such as sunlight or light of a mercury lamp and resumes its initial color (fading of color) when it is no longer irradiated with light but is placed in a dark place. The compound having this property is called photochromic compound. One of the uses of the photochromic compound may be to use it as a dimmer material for lenses of sunglasses.

In such an application, the photochromic compound must have photochromic properties which are, for example:

(1) Color changes stably when the developing of color and the fading of color are repeated (has a good repetitive color resistance);
(2) Has a small coloring degree (hereinafter called initial color) when placed in a state of not being irradiated with light; and
(3) Exhibits a high color fading rate when the compound is no longer irradiated with light.

In recent years, it has been urged to produce a photochromic compound which, by itself, develops a neutral tint such as gray, brown or green. The compound that develops a neutral tint must have two absorption bands (440 to 550 nm and 580 to 630 nm) in a wavelength region of visible light, and must have nearly the same absorption intensity ratio in each absorption band.

In order to satisfy the above requirement, a variety of photochromic compounds have heretofore been synthesized without, however, any particular common nature in their structures.

For example, U.S. Pat. No. 5,783,116 discloses a chromene compound represented by the following formula (A),

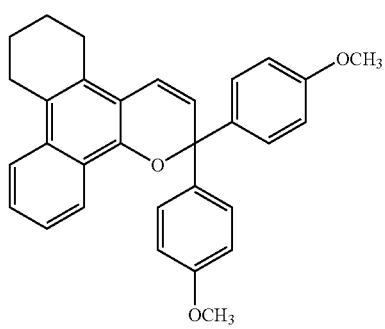

(A)

This chromene compound has only one absorption band and is not capable of developing color tone of a neutral tint and, further, has a problem of a small color fading rate.

Further, PCT Laid-Open WO 00/15628 discloses a chromene compound represented by the following formula (B),

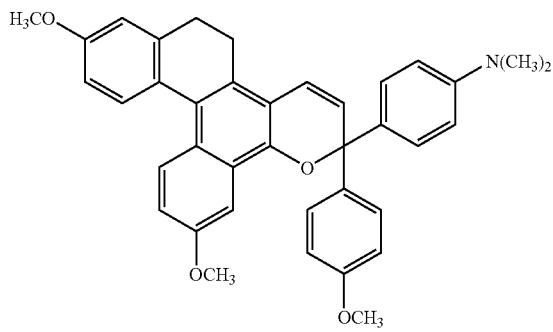

(B)

This chromene compound satisfies the requirement of a color-developing spectrum of a neutral tint described above, and is capable of developing a neutral tint such as brown offering such a feature that the initial coloring is weak accompanied, however, by a defect of low color fading rate.

Japanese Patent Application No. 344762/2000 discloses a chromene compound represented by the following formula (C),

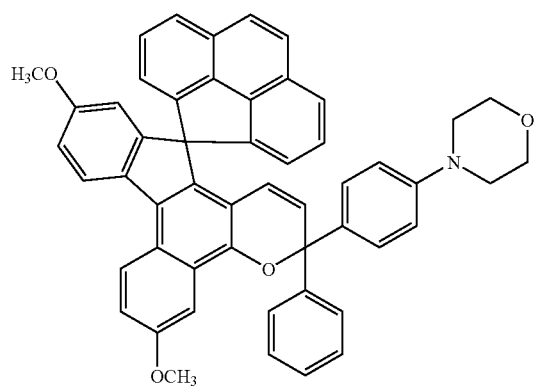

(C)

This chromene compound exhibits a high color fading rate but has a large difference in the absorption intensity between the two absorption bands. Therefore, this chromene compound develops a single color of blue only accompanied by a defect of large initial coloring.

DISCLOSURE OF THE INVENTION

It is therefore an object of the present invention to provide a novel chromene compound which exhibits a weak initial color, a large color fading rate and develops a color tone of a neutral tint by solving the above-mentioned problems inherent in the conventional known compounds.

That is, according to the present invention, there is provided a chromene compound represented by the following general formula (1),

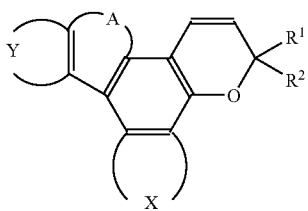
(1)

wherein $R^1$ and $R^2$ are, independently from each other, alkyl groups, aryl groups which may have a substituent, or heteroaryl groups which may have a substituent, and $R^1$ and $R^2$ together may constitute a ring, groups represented by,

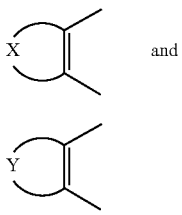

(1a)

and (1b)

are, independently from each other, divalent aromatic hydrocarbon groups or divalent aromatic heterocyclic groups which may have a substituent, and a group represented by

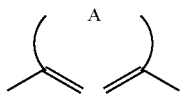

(1c)

is represented by the following formula (1c-1) or (1c-2),

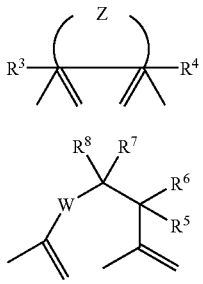

(1c-1)

(1c-2)

wherein in the formula (1c-1), the group represented by,

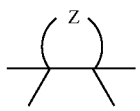

is a tetravalent alicyclic hydrocarbon group or a tetravalent heterocyclic group, which may have a substituent, $R^3$ and $R^4$ are, independently from each other, hydrogen atoms, hydroxyl groups, alkyl groups, alkoxy groups, aralkyl groups, aralkoxy groups, amino groups, substituted amino groups, cyano groups, nitro groups, halogen atoms, halogenoalkyl groups, halogenoalkoxy groups or substituted or unsubstituted alicyclic hydrocarbon groups, and in the above formula (1c-2), $R^5$, $R^6$, $R^7$ and $R^8$ are, independently from each other, hydrogen atoms, hydroxyl groups, alkyl groups, cycloalkyl groups, alkoxy groups, aralkyl groups, aralkoxy groups, amino groups, substituted amino groups, cyano groups, nitro groups, substituted or unsubstituted aryl groups, substituted or unsubstituted heteroaryl groups, halogen atoms, halogenoalkyl groups or halogenoalkoxy groups, and two groups out of $R^5$ to $R^8$ may be combined together to form a ring, and W is a group represented by,

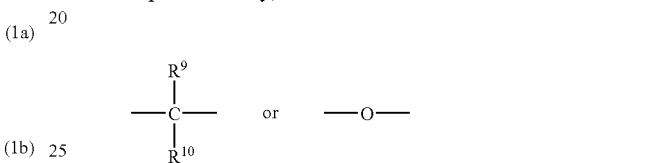

wherein $R^9$ and $R^{10}$ are, independently from each other, hydrogen atoms, hydroxyl groups, alkyl groups, cycloalkyl groups, alkoxy groups, aralkyl groups, aralkoxy groups, amino groups, substituted amino groups, cyano groups, nitro groups, substituted or unsubstituted aryl groups, substituted or unsubstituted heteroaryl groups, halogen atoms, halogenoalkyl groups or halogenoalkoxy groups.

According to the present invention, further, there are provided a photochromic material comprising a chromene compound represented by the above general formula (1), and a photochromic optical material containing the chromene compound.

BEST MODE FOR CARRYING OUT THE INVENTION

Figure 1:
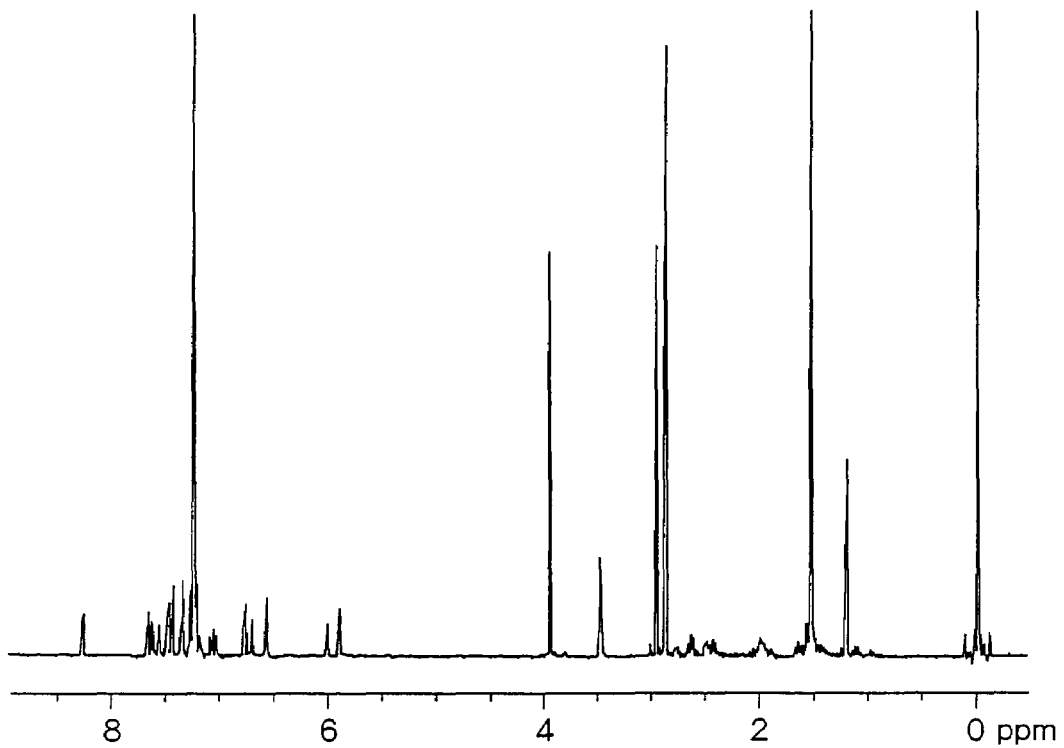
FIGS. 1 and 2 are diagrams illustrating proton nuclear magnetic resonance spectra of chromene compounds synthesized in Examples 1 and 37.

In the above-mentioned general formula (1), groups represented by the formulas (1a) and (1b),

(1a)

(1b)

are, independently from each other, divalent aromatic hydrocarbon groups or divalent aromatic heterocyclic groups which may have a substituent.

Though there is no particular limitation, it is desired that the above aromatic hydrocarbon groups have carbon atoms in a number in a range of from 6 to 18 without including those of the substituents. Preferred examples of the aromatic hydrocarbon group include phenylene group, naphthylene group, phenanthrene group, tolylene group or xylylene group having one benzene ring, or those having a condensed ring condensed with 2 to 4 benzene rings.

Though there is no particular limitation, it is desired that the aromatic heterocyclic rings are those comprising a heterocyclic ring such as a 5-membered ring or a 6-membered ring including an oxygen atom, a sulfur atom or a nitrogen atom; a condensed heterocyclic ring in which a benzene ring or a heterocyclic ring is condensed with the above-mentioned heterocyclic ring; or a condensed heterocyclic ring in which a heterocyclic ring is condensed with an aromatic hydrocarbon ring such as benzene ring. Preferred examples of the aromatic heterocyclic group include nitrogen-containing heterocyclic groups such as pyridylene group, quinolylene group, pyrrolylene group and indolylene group; oxygen-containing heterocyclic groups such as furylene group and benzofurylene group; and sulfur-containing heterocyclic groups such as thienylene group and benzothienylene group.

Further, the above-mentioned aromatic hydrocarbon groups and the aromatic heterocyclic groups may have a substituent (hereinafter abbreviated as R). As the substituent (R), there can be exemplified the following ones.

Namely, hydroxyl group, alkyl group, cycloalkyl group, alkoxy group, aralkyl group, aralkoxy group, amino group, substituted amino group, cyano group-, nitro group, substituted or unsubstituted aryl group, halogen atom, halogenoalkyl group, halogenoalkoxy group, and substituted or unsubstituted heterocyclic group having a nitrogen atom as a hetero atom and is bonded to the above aromatic hydrocarbon group or to the aromatic heterocyclic group through the nitrogen atom.

The substituent (R) exemplified above will now be described.

Though there is no particular limitation, the alkyl group is usually the one having 1 to 4 carbon atoms. Preferred examples of the alkyl group include methyl group, ethyl group, n-propyl group, isopropyl group, n-butyl group, sec-butyl group and tert-butyl group.

Though there is no particular limitation, the cycloalkyl group is usually the one having 3 to 12 carbon atoms. Preferred examples of the cycloalkyl group include cyclopropyl group, cyclobutyl group, cyclopentyl group, cyclohexyl group, cycloheptyl group and cyclooctyl group.

Though there is no particular limitation, the alkoxy group is usually the one having 1 to 5 carbon atoms. Concrete examples of the alkoxy group include methoxy group, ethoxy group, n-propoxy group, isopropoxy group, n-butoxy group, sec-butoxy group and tert-butoxy group.

Though there is no particular limitation, the aralkyl group is usually the one having 7 to 11 carbon atoms. Preferred examples of the aralkyl group include benzyl group, phenylethyl group, phenylpropyl group and phenylbutyl group.

Though there is no particular limitation, the aralkoxy group is preferably the one having 6 to 10 carbon atoms. Concrete examples of the aralkoxy group include phenoxy group and naphthoxy group.

Though there is no particular limitation, the substituted amino group is the group such as alkylamino group, dialkylamino group, arylamino group or diarylamino group for which alkyl group or aryl group is substituted. Concrete examples of the substituted amino group include methylamino group, ethylamino group, phenylamino group, dimethylamino group, diethylamino group and diphenylamino group.

Though there is no particular limitation, the unsubstituted aryl group is the one having 6 to 14 carbon atoms, such as phenyl group and naphthyl group.

Though there is no particular limitation, the unsubstituted heteroaryl group is the one containing oxygen, sulfur or nitrogen atom as a hetero atom, and having 4 to 12 atoms for forming a ring. Preferred examples of the heteroaryl group include thienyl group, furyl group, pyrrolynyl group, pyridyl group, benzothienyl group, benzofuranyl group, benzopyrrolynyl group and eurolidino group.

As the substituent possessed by the substituted aryl group and the substituted heteroaryl group, i.e., as the group substituted by one or more hydrogen atoms of the unsubstituted aryl group or of the unsubstituted heteroaryl group, their can be exemplified those similar to the groups exemplified in connection with the substituent (R).

As the halogen atom, there can be exemplified fluorine atom, chlorine atom, bromine atom and iodine atom.

As the halogenoalkyl group, there can be exemplified the one in which one or more hydrogen atoms of the above-mentioned alkyl group are substituted by fluorine atoms, chlorine atoms or bromine atoms. Preferred examples of the halogenoalkyl group include fluoromethyl group, difluoromethyl group and trifluoromethyl group.

As the halogenoalkoxy group, there can be exemplified the one in which one or more hydrogen atoms of the alkoxy group are substituted by fluorine atoms, chlorine atoms or bromine atoms. Particularly preferred examples of the halogenoalkoxy group include fluoromethoxy group, difluoromethoxy group and trifluoromethoxy group.

There is no particular limitation on the heterocyclic group which is the substituent (R) so far as it has a nitrogen atom as a hetero atom and is bonded to the ring of the aromatic hydrocarbon group or of the aromatic heterocyclic group through the nitrogen atom. The number of carbon atoms constituting the heterocyclic ring as the substituent (R) is, generally, from 2 to 10 and, particularly preferably, from 2 to 6. Further, the heterocyclic ring which is the substituent (R) may include hetero atoms such as oxygen atom, sulfur atom and nitrogen atom in addition to the nitrogen atom bonded to the ring of the aromatic hydrocarbon group or of the aromatic heterocyclic group. The heterocyclic ring as the substituent (R) may further include a substituent (as this substituent, there can be exemplified those which are the same as the ones exemplified in connection with the substituent (R)).

Preferred examples of the heterocyclic group as the substituent (R) include morpholino group, pipelidino group, pyrrolidinyl group, piperadino group, N-methylpiperadino group and indolinyl group.

In the present invention, particularly preferred examples of the above-mentioned substituent (R) include alkyl group, alkoxy group, aralkyl group, amino group, substituted amino group, halogenoalkyl group and substituted or unsubstituted heterocyclic group having a nitrogen atom as a hetero atom and is bonded through the nitrogen atom.

There is no particular limitation on the positions to where the above-mentioned substituents (R) are bonded and the total number thereof. Generally, however, the number thereof is 0 to 3 and, preferably, not larger than 2. When there are present two or more substituents (R), these substituents (R) may be different from one another or may be the same.

In the above general formula (1), the groups represented by the formula (1c),

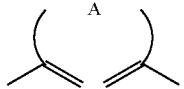

can be divided into those represented by the following formula (1c-1) and those of the following formula (1c-2),

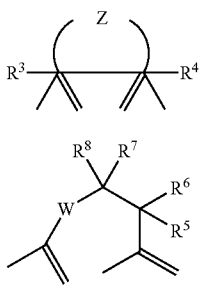

In the present invention, the group represented by the formula (1c-1) or (1c-2) is bonded to a predetermined position of a skeleton of the compound represented by the general formula (1) accounting for an excellent color fading rate, strong absorption bands in the two wavelength regions of from 440 to 500 nm and from 570 to 630 nm, and developing a favorable neutral tint.

Described below are the groups represented by the formulas (1c-1) and (1c-2).

First, in the formula (1c-1), the group (hereinafter often referred to simply as group (Z)) represented by the following formula;

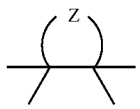

is a substituted or unsubstituted tetravalent alicyclic hydrocarbon group or a substituted or unsubstituted tetravalent heterocyclic group.

The aliphatic ring possessed by the above tetravalent alicyclic hydrocarbon group may be, for example, a monocyclic ring or a crosslinking ring such as a bicyclo ring without any limitation.

The monocyclic ring, preferably has 3 to 20 carbon atoms, and its examples include cyclopropyl ring, cyclobutyl ring, cyclopentyl ring, cyclohexyl ring, cycloheptyl ring, cyclooctyl ring, cyclononyl ring, cyclodecyl ring, cycloundecyl ring, cyclododecyl ring, cyclotridecyl ring and cyclopentadodecyl ring. The crosslinking ring, preferably, has 6 to 20 carbon atoms, and its examples include, bicyclo[2,2,1]heptane, bicyclo[2,2,2]octane, bicyclo[3,2,0]heptane, bicyclo[3,1,1]heptane, bicyclo[3,2,1]octane, bicyclo[3,3,1]nonane, bicyclo[3,3,2]decane, bicyclo[3,3,3]undecane, bicyclo[4,2,2]decane, bicyclo[4,3,2]undecane, bicyclo[4,3,3]dodecane, bicyclo[4,1,0]heptane, bicyclo[4,1,1]octane, bicyclo[4,2,1]nonane, bicyclo[4,2,0]octane, bicyclo[4,4,0]decane, octahydroindene, bicyclo[4,3,1]dodecane, decahydro-naphthalene, decahydro-benzocyclononane, tricycloheptane, dodecahydro-phenalene, dodecahydro-cyclopentapentalene, dodecahydro-fluorene, tetradecahydro-anthracene, tricylododecane and tricyclopentadecane.

In the tetravalent alicyclic hydrocarbon group comprising the crosslinked ring, there is no particular limitation on the positions of the four coupling hands so far as the two coupling hands are positioned on the two neighboring carbon atoms and the crosslinked ring is incorporated in the chromene compound of the general formula (1) as a structure represented by the formula (1c-1); i.e., the positions of the coupling hands may be at the head of the bridge or at any other positions of the ring.

As the substituent for these alicyclic hydrocarbon groups, there can be used the same groups as those exemplified in connection with the above-mentioned substituent (R) without any limitation. Further, the monocyclic group may have a group to which a cycloalkyl group is spiro-union. There is no particular limitation on the position and number of these substituents. In general, however, the number thereof is from 0 to 3 and, desirably, not larger than 2. When 2 or more substituents are bonded, such substituents may be different from one another or may be the same.

As the heterocyclic ring possessed by the tetravalent heterocyclic group, there can be used the monocyclic rings exemplified in the above alicyclic hydrocarbon groups, in which 1 or more and, preferably, 1 or 2 methylene groups are substituted with at least one kind of group selected from the group consisting of imino group (—NR'—; R' is a hydrogen atom, an alkyl group or an aryl group), oxy group (—O—), thio group (—S—), carbonyl group (—CO—), carbonyloxy group (—COO—) and amide group (—NHCO—). As the crosslinking ring exemplified in the above alicyclic hydrocarbon groups, there can be exemplified those groups in which 1 or more and, preferably, 1 or 2 methylene groups are substituted by the above-mentioned groups, or those in which 1 or more and, preferably, 1 or 2 methylidene groups of the crosslinking ring are substituted by the nitrilo groups (=N—). Among these heterocyclic rings, the rings having imino group (—NR'—) or oxy group (—O—) are preferable.

Concretely speaking, there can be exemplified the following heterocyclic rings.

Oxygen-containing rings such as tetrahydrofuran ring and pyran ring; nitrogen-containing rings such as pyrrolidine ring, piperidine ring, morpholine ring, thiomorpholine ring, piperadine ring, and hexamethyleneimine ring; carbonyl-containing rings such as cyclopentanone ring and cyclohexanone ring; ester-containing rings or oxygen-containing carbonyl mixed rings such as butylolactone ring, tetrahydrofuranone ring and tetrahydropyranone ring; amide-containing rings or nitrogen-containing carbonyl mixed Spiro rings such as pyrrolidinone ring, piperidinone ring and oxohexamethyleneimine ring; and crosslinked rings such as aza-bicyclo[2,2,2]octane ring, decahydro-cyclopentaazepin ring, aza-bicyclo[3,2,1]octane ring, octahydro-quinolidine ring, decahydro-pyridinoquinoline ring and aza-tricycloundacane ring.

The heterocyclic group comprising the above-mentioned heterocyclic ring may have a substituent like the above-mentioned alicyclic hydrocarbon groups. The substituent may be the same as those substituents exemplified in connection with the alicyclic hydrocarbon groups.

As described above, the group (z) included in the group of the formula (1-c) is an alicyclic hydrocarbon group or a heterocyclic group. In either case, it is desired that the group has 6 to 12 carbon atoms for forming a ring when it is a monocyclic group from the standpoint of improving the color fading rate and easy synthesis. When it is the crosslinking cyclic group, it is desired that the group has atoms in a total number of 6 to 18 for forming the ring. When it is the monocyclic group, further, it is particularly desired that the group has 1 to 5 alkyl groups with 1 to 4 carbon atoms as substituents. When it is the crosslinking cyclic group, it is particularly desired that the group has 1 to 6 alkyl groups with 1 to 4 carbon atoms as substituents.

It is further desired that the group (z) is an alicyclic hydrocarbon group and, most desirably, a monocyclic ring such as cyclohexylene group, cycloheptylene group, cyclooctylene group or cyclododecylene group, or the above monocyclic ring which has 1 to 4 alkyl groups such as methyl groups, ethyl groups or propyl groups, or a crosslinked aliphatic hydrocarbon ring such as bicyclo[2,2,1]heptane, bicyclo[3,2,1]octane or decahydro-naphthalene.

In the formula (1c-1), $R^3$ and $R^4$ are, independently from each other, hydrogen atoms, hydroxyl groups, alkyl groups, alkoxy groups, aralkyl groups, aralkoxy groups, amino groups, substituted amino groups, cyano groups, nitro groups, halogen atoms, halogenoalkyl groups, halogenoalkoxy groups, or substituted or unsubstituted alicyclic hydrocarbon groups. Among these groups, the groups duplicating those described as the above-mentioned groups (R) have the same meanings.

As the substituted or unsubstituted alicyclic hydrocarbon group, there can be exemplified monovalent groups corresponding to the tetravalent alicyclic hydrocarbon groups described in connection with the above-mentioned group (z).

In the present invention, $R^3$ and $R^4$ are preferably hydrogen atoms; alkyl groups such as methyl group, ethyl group and propyl group; alkoxy groups such as methoxy group, ethoxy group and propoxy group; aralkyl groups such as benzyl group, phenylethyl group, phenylpropyl group and phenylbutyl group; aralkoxy groups such as phenoxy group and naphthoxy group; substituted amino groups such as methylamino group, ethylamino group, phenylamino group, dimethylamino group, diethylamino group and diphenylamino group; halogen atoms such as fluorine atom, chlorine atom, bromine atom and iodine-atom; halogenoalkyl groups such as trifluoromethyl group and the like group; halogenoalkoxy groups such as trifluoromethoxy group and the like group; and alicyclic hydrocarbon groups having a monocyclic ring with 3 to 12 carbon atoms, such as cyclopropyl group, cyclobutyl group, cyclopentyl group, cyclohexyl group, cycloheptyl group and cyclooctyl group. There can be further preferably used the following alicyclic hydrocarbon groups comprising crosslinking aliphatic rings with 6 to 20 carbon atoms. That is, bicyclo[2,2,1]heptane, bicyclo[2,2,2]octane, bicyclo[3,2,0]heptane, bicyclo[3,1,1]heptane, bicyclo[3,2,1]octane, bicyclo[3,3,1]nonane, bicyclo[3,3,2]decane, bicyclo[3,3,3]undecane, bicyclo[4,2,2]decane, bicyclo[4,3,2]undecane, bicyclo[4,3,3]dodecane, bicyclo[4,1,0]heptane, bicyclo[4,1,1]octane, bicyclo[4,2,1]nonane, bicyclo[4,2,0]octane, octahydroindene, bicyclo[4,3,1]dodecane, decahydro-naphthalene, decahydro-benzocyclononane, tricycloheptane, dodecahydro-phenalene, dodecahydro-cyclopentapentalene, dodecahydro-fluorene, tetradecahydro-anthracene, tricyclododecane and tricyclopentadecane.

In the present invention, $R^3$ and $R^4$ are most preferably hydrogen atoms, alkyl groups and halogen atoms.

Next, in the above formula (1c-2), W is a group represented by,

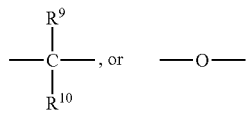

wherein $R^9$ and $R^{10}$ are, independently from each other, hydrogen atoms, hydroxyl groups, alkyl groups, cycloalkyl groups, alkoxy groups, aralkyl groups, aralkoxy groups, amino groups, substituted amino groups, cyano groups, nitro groups, substituted or unsubstituted aryl groups, substituted or unsubstituted heteroaryl groups, halogen atoms, halogenoalkyl groups or halogenoalkoxy groups, which are the same as those groups described above as the substituents (R).

In the above formula (1c-2), further, $R^5$, $R^6$, $R^7$ and $R^8$ are, independently from each other, hydrogen atoms, hydroxyl groups, alkyl groups, cycloalkyl groups, alkoxy groups, aralkyl groups, aralkoxy groups, amino groups, substituted amino groups, cyano groups, nitro groups, substituted or unsubstituted aryl groups, halogen atoms, halogenoalkyl groups or halogenoalkoxy groups. Among these groups, those duplicating the above-mentioned groups (R) have the same meanings.

Among the groups $R^5$, $R^6$, $R^7$ and $R^8$ in the invention, the groups $R^5$ and $R^6$ affect the color fading rate due to their steric hindrance and must, hence, be larger than hydrogen atom.

Further, $R^5$ and $R^6$ together, or $R^7$ and $R^8$ together, may form a ring. Further, either one of $R^5$ or $R^6$ and either one of $R^7$ or $R^8$ may be combined together to form a ring. Such rings may be aliphatic rings, aromatic rings or heterocyclic rings. Though there is no particular limitation on the structure of the rings, concrete examples are as described below.

As the aliphatic ring and heterocyclic ring, there can be exemplified those aliphatic rings and heterocyclic rings that were exemplified concerning the alicyclic hydrocarbon groups and aromatic heterocyclic groups of the above group (z). As the aromatic hydrocarbon ring, there can be exemplified fluorene and phenanthrene.

These rings may have a substituent as a matter of course. There is no particular limitation on the substituent. For example, the substituent may be alkyl group, cycloalkyl group, alkoxy group, amino group, substituted amino group, substituted or unsubstituted aralkyl group, or substituted or unsubstituted aryl group, that were exemplified concerning the above-mentioned substituent (R). There is no particular limitation, either, on the positions and number of the substituents.

In the present invention, particularly preferred groups $R^5$, $R^6$, $R^7$ and $R^8$ represented by the formula (1c-2) are hydrogen atoms or alkyl groups having 1 to 4 carbon atoms. Or, two groups out of the groups $R^5$ to $R^8$ may be combined together to form a ring. Further, W is a group represented by,

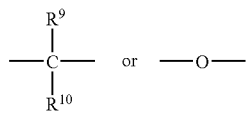

wherein $R^9$ and $R^{10}$ are, independently from each other, hydrogen atoms or alkyl groups having 1 to 4 carbon atoms.

Reverting to the above general formula (1), $R^1$ and $R^2$ are, independently from each other, alkyl groups, substituted or unsubstituted aryl groups or substituted or unsubstituted heteroaryl groups. These groups $R^1$ and $R^2$ together may constitute a ring.

Here, the alkyl groups, substituted or unsubstituted aryl groups and substituted or unsubstituted heteroaryl groups are the same as the groups described concerning the above group R.

The ring formed by $R^1$ and $R^2$ in combination may be any one of aliphatic hydrocarbon ring, heterocyclic ring or aromatic hydrocarbon ring. Though there is no particular limitation, the aliphatic hydrocarbon ring is preferably a crosslinked ring having 6 to 18 carbon atoms, such as bicyclo[2,2,1]heptane ring, bicyclo[2,2,2]octane ring, bicyclo[3,2,1]octane ring or bicyclo[3,3,1]nonane ring, the heterocyclic ring is preferably a crosslinking ring having 6 to 18 carbon atoms, such as aza-bicyclo[2,2,2]octane ring, decahydro-cyclopentaazepin ring or aza-bicyclo[3,2,1]octane ring, and the aromatic hydrocarbon ring is preferably the one having 10 to 18 carbon atoms, such as fluorene ring or phenanthrene ring.

The ring formed by $R^1$ and $R^2$ together may have a substituent as represented by alkyl group, alkoxy group, aryl group, hydroxyl group or halogen atom. Here, the alkyl group, alkoxy group, aryl group and halogen atom are the same as those described concerning the above-mentioned substituents (R).

In the present invention, it is particularly desired that at least either $R^1$ or $R^2$ is any one of the following groups (i) to (iii):

(i) a substituted aryl group having a substituted amino group or an alkoxy group as a substituent;

(ii) a substituted aryl group having, as a substituent, a substituted or unsubstituted heterocyclic ring which has a nitrogen atom as a hetero atom and is bonded through the nitrogen atom; or (iii) a substituted aryl group having, as a substituent, a condensed heterocyclic ring in which the heterocyclic ring having a nitrogen atom as the hetero atom in (ii) above is condensed with an aromatic hydrocarbon ring or with an aromatic heterocyclic ring.

In the substituted aryl groups of (i) to (iii) above, there is no particular limitation on the positions and number of the substituents. It is, however, desired that the substituent is located at the third position or at the fourth position when the aryl group is a phenyl group and that the number of the substituent is one. Concrete examples of the substituent phenyl group include 4-(N,N-dimethylamino)phenyl group, 4-(N,N-diethylamino)phenyl group, 4-(N,N-diphenylamino)phenyl group, 4-morpholinophenyl group, 4-piperidinophenyl group, and 3-(N,N-dimethylamino)phenyl group.

When the aryl group is the one other than phenyl group in (i) to (iii) above, there is no particular limitation on the positions and number of the substituents. Generally, however, it is desired that the number of the substituent is 1. Preferred examples of the substituted aryl group include 4-(N,N-dimethylamino)thienyl group, 4-(N,N-diethylamino)furyl group, 4-(N,N-diphenylamino)thienyl group, 4-morpholinopyrrolinyl group, 6-piperidinobenzothienyl group and 6-(N,N-dimethylamino)benzofuranyl group.

In the present invention, further, $R^1$ and $R^2$ may be eurolidino groups to be competitive to the above groups (i) to (iii).

Among the chromene compounds represented by the above general formula (1), those compounds which are particularly desired from the standpoint of effect are described below being divided into those having groups represented by the above formula (1c-1) and those having groups represented by the above formula (1c-2). In the following formula, the symbols same as those described in connection with the general formula (1) have the meanings as described in connection with the general formula (1).

The chromene compound having the group represented by the formula (1c-1) is desirably the one represented by the following general formula (2),

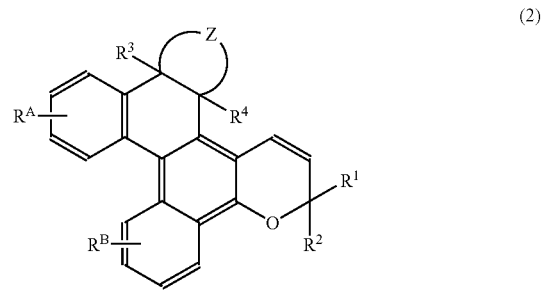

(2)

In the above general formula (2), $R^A$ and $R^B$ have the same meanings as the substituents (R) that were described already.

In the chromene compound of the above general formula (2), it is particularly desired that the substituent $R^B$ is coupled to the positions shown below from the standpoint of color density and color fading rate.

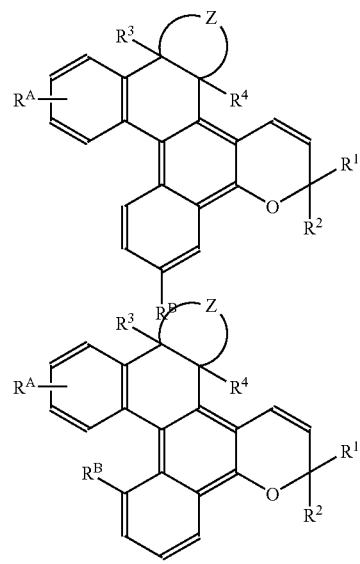

Though not limited thereto only, concrete examples of the chromene compound of the general formula (2) include those of the following formulas (2a) to (2c).

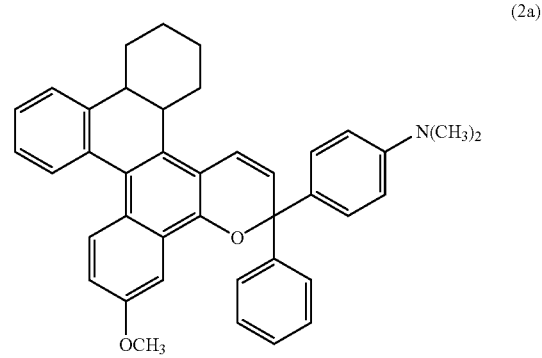

(2a)

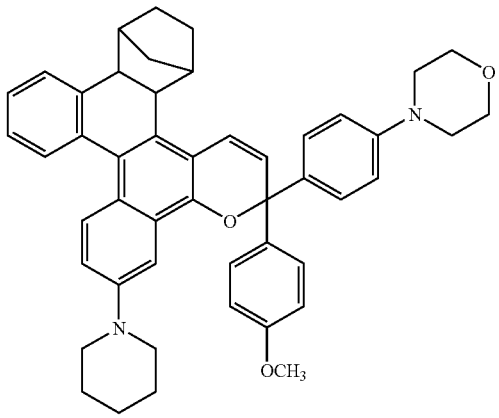
(2b)

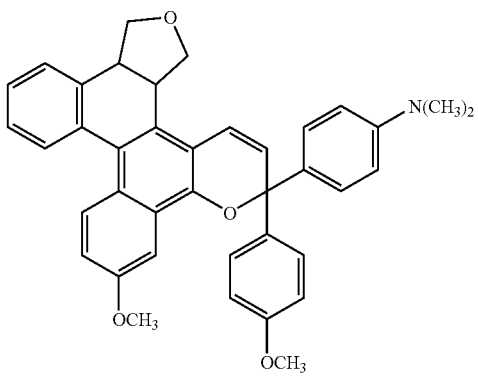
(2c)

The chromene compound having a group represented by the formula (1c-2) is desirably the one represented by the following general formula (3):

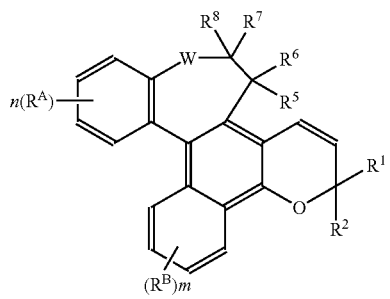
(3)

In the above general formula (3), $R^A$ and $R^B$ are the same as the substituents (R) described already, and n and m are integers of 0 to 2, respectively.

In the chromene compound of the above general formula (3), there is no particular limitation on the positions where the substituents $R^A$ and $R^B$ are bonded. From the standpoint of color density and color fading rate, however, it is particularly desired that the substituents are bonded to the positions shown in the following formulas,

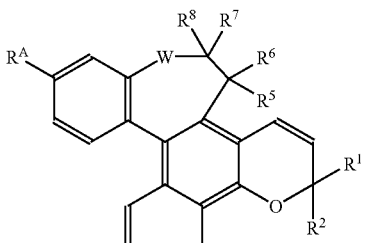

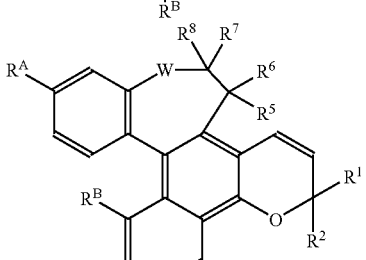

Though not limited thereto only, concrete examples of the chrome compound of the general formula (3) can be represented by the following formulas (3a) to (3c).

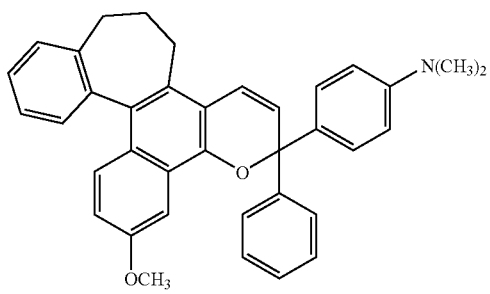
(3a)

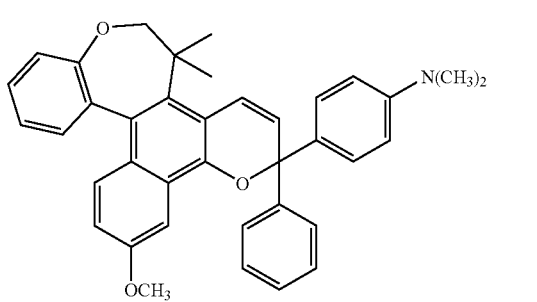
(3b)

(3c)

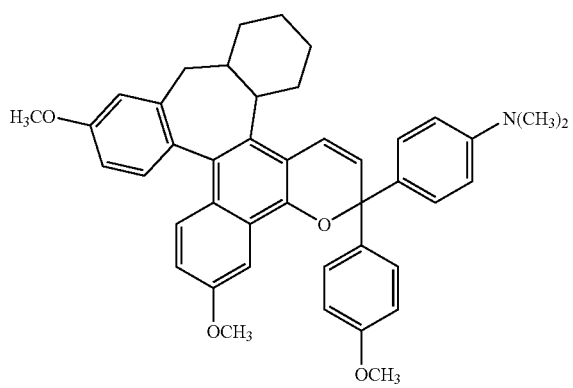

The chromene compound represented by the above general formula (1) of the present invention usually exists as a colorless or pale bluish solid or viscous liquid at normal temperature and under normal pressure, and can be confirmed by the following means (a) to (c).

(a) Measurement of a proton nuclear magnetic resonance spectrum ($^1$H-NMR) indicates peaks based on an aromatic proton and an alkene proton near δ 5.9 to 9.0 ppm and peaks based on an alkyl group and an alkylene group near δ 1.0 to 4.0 ppm. Upon relatively comparing the spectrum intensities, further, the numbers of protons in the bonding groups can be known.

(b) The compositions of the corresponding products can be determined by the elemental analysis.

(c) Measurement of a $^{13}$C-nuclear magnetic resonance spectrum ($^{13}$C-NMR) indicates a peak based on a carbon atom of an aromatic hydrocarbon group near δ 110 to 160 ppm, a peak based on a carbon atom of an alkene near δ 80 to 140 ppm, and peaks based on carbon atoms of an alkyl group and an alkylene group near δ 20 to 80 ppm.

The chromene compound of the present invention can be synthesized by a variety of methods. Among them, a particularly preferred preparation method is as described below.

A naphthol derivative represented by the following general formula (4), (4)

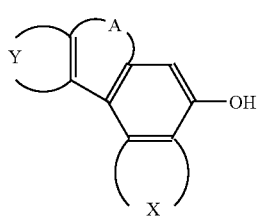

is reacted with a propargyl alcohol derivative represented by the following general formula (5), (5)

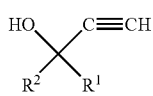

in the presence of an acid catalyst to obtain a chromene compound of the above general formula (1). In the above general formulas (4) and (5), $R^1$, $R^2$, X, Y and Z are as defined in the above general formula (1).

There is no particular limitation on the reaction ratio of the naphthol derivative and the propargyl alcohol derivative. Generally, however, the reaction ratio is selected over a range of from 1:10 to 10:1 (mol ratio).

As the acid catalyst, there can be used sulfuric acid, benzenesulfonic acid, p-toluenebenzenesulfonic acid and acidic alumina. The acid catalyst is used in an amount over a range of from 0.1 to 10 parts by weight per 100 parts by weight of the total amount of the naphthol derivative and the propargyl alcohol derivative.

The reaction temperature is desirably from 0 to 200° C. The reaction is carried out in a nonprotonic organic solvent such as N-methylpyrrolidone, dimethylformamide, tetrahydrofuran, benzene or toluene.

The thus obtained chromene compound of the present invention dissolves well in a general organic solvent such as toluene, chloroform or tetrahydrofuran. When the chromene compound is dissolved in such a solvent, the solution generally remains nearly colorless and transparent exhibiting a very weak initial color. When irradiated with the sunlight or ultraviolet rays, the solution quickly develops a color. When the light is shut off, the solution quickly returns back to the initial colorless state, thus exhibiting a reversible photochromic action.

The above photochromic action of the chromene compound of the present invention is similarly exhibited even in a high molecular solid matrix. There is no particular limitation on the high molecular solid matrix provided it permits the chromene compound of the present invention to be homogeneously dispersed therein. Optically preferred examples of the high molecular solid matrix include thermoplastic resins such as poly(methyl acrylate), poly(ethyl acrylate), poly(methyl methacrylate), poly(ethyl methacrylate), polystyrene, polyacrylonitrile, polyvinyl alcohol, polyacrylamide, poly(2-hydroxyethyl methacrylate), polydimethyl siloxane, polyethylene glycol monoallyl ether, polycarbonate, etc.

In addition to the above-mentioned thermoplastic resins, there can be used, as high molecular solid matrixes, thermosetting resins obtained by polymerizing the following radically polymerizable polyfunctional monomers.

Radically Polymerizable Polyfunctional Monomers:

Ester compounds of multi-valent acrylic acid and multi-valent methacrylic acid, such as ethylene glycol diacrylate, diethylene glycol dimethacrylate, triethylene glycol dimethacrylate, tetraethylene glycol dimethacrylate, ethylene glycol bisglycidyl methacrylate, bisphenol A dimethacrylate, 2,2-bis(4-methacryloyloxyethoxyphenyl)propane, and 2,2-bis(3,5-dibromo-4-methacryloyloxyethoxyphenyl)propane;

multi-valent allyl compounds such as diallyl phthalate, diallyl terephthalate, diallyl isophthalate, diallyl tartarate, diallyl epoxysuccinate, diallyl fumarate, diallyl chloroendoate, diallyl hexaphthalate, diallyl carbonate, allyl diglycol carbonate, and trimethylolpropanetriallyl carbonate;

ester compounds of multi-valent thioacrylic acid and multi-valent thiomethacrylic acid, such as 1,2-bis(methacryloylthio)ethane, bis(2-acryloylthioethyl)ether, and 1,4-bis(methacryloylthiomethyl)benzene;

ester compounds of acrylic acid and ester compounds of methacrylic acid, such as glycidyl acrylate, glycidyl methacrylate, β-methylglycidyl methacrylate, bisphenol A-monoglycidyl ether methacrylate, 4-glycidyloxymethacrylate, 3-(glycidyl-2-oxyethoxy)-2-hydroxypropyl methacrylate, 3-(glycidyloxy-1-isopropyloxy)-2-hydroxypropyl acrylate, and 3-glycidyloxy-2-hydroxypropyloxy)-2-hydroxypropyl acrylate; and divinyl benzene.

It is also allowable to use copolymers of the monomers exemplified above and the following comonomers.

Comonomers:

Unsaturated carboxylic acids such as acrylic acid, methacrylic acid and anhydrous maleic acid;

ester compounds of acrylic acid and methacrylic acid, such as methyl acrylate, methyl methacrylate, benzyl methacrylate, phenyl methacrylate and 2-hydroxyethyl methacrylate;

ester compounds of fumaric acid, such as diethyl fumarate and diphenyl fumarate;

ester compounds of thioacrylic acid and thiomethacrylic acid, such as methylthioacrylate, benzylthioacrylate and benzylthiomethacrylate; and vinyl compounds such as styrene, chlorostyrene, methylstyrene, vinylnaphthalene, α-methylstyrene dimer and bromostyrene.

There is no particular limitation on the method of dispersing the chromene compound of the present invention in the high molecular solid matrix, and a generally accepted method can be used. For example, a method in which the thermoplastic resin and the chromene compound are kneaded together in a molten state so as to be dispersed in the resin, a method in which the chromene compound is dissolved in the polymerizable monomer and, after a polymerization catalyst is added thereto, is polymerized with heat or light so as to be dispersed in the resin, or a method in which the surfaces of the thermoplastic resin and of a thermosetting resin are dyed with the chromene compound so that the chromene compound is dispersed in the resins.

The chromene compound of the present invention can be used as a photochromic material over a wide range applications, such as various memory materials to substitute for the silver salt photosensitive material, copying material, photosensitive material for printing, memory material for cathode-ray tubes, photosensitive material for laser and photosensitive material for holography. Further, the photochromic material using the chromene compound of the present invention can be used as a photochromic lens material, optical filter material, display material, actinometer, ornament, etc. When used as a photochromic lens, for example, there is no particular limitation provided a uniform dimming performance is obtained. Concretely speaking, there can be exemplified a method in which a polymer film containing the photochromic material of the invention homogeneously dispersed therein is sandwiched in the lens, a method in which the chromene compound of the invention is dispersed in the polymerizable monomer and is polymerized in a predetermined manner, and a method in which the compound is dissolved in, for example, a silicone oil so that the lens surfaces are impregnated with the compound at 150 to 200° C. for 10 to 60 minutes, and the surfaces are further coated with a curable material to form a photochromic lens. There can be further exemplified a method in which the polymer film is applied onto the lens surfaces which are, then, coated with a curable material to form a photochromic lens.

The chromene compound of the present invention exhibits a high color fading rate in a solution or in a high molecular solid matrix. It further exhibits weak coloring degree in a state of not being irradiated with light, is little colored even after it is aged and exhibits good photochromic light resistance. For example, the photochromic lens using the chromene compound of the invention quickly resumes its initial color tone when it is brought indoors from the outdoors, is colored little even after it is used for extended periods of time and is aged and, further, exhibits good light resistance.

Further, when placed in a state of developing color, the chromene compound of the invention exhibits absorption bands in the two wavelength regions of 440 to 500 nm and 570 to 630 nm. Besides, a difference in the absorption intensity is small between the two absorption bands, and the intensity ratio of the color densities in the two absorption bands is usually in a range of from 0.7 to 1.2. Therefore, a color tone of neutral tint such as grey or brown is obtained by using a single compound.

EXAMPLES

Example 1

6.6 Grams (0.02 mols) of the following naphthol derivative

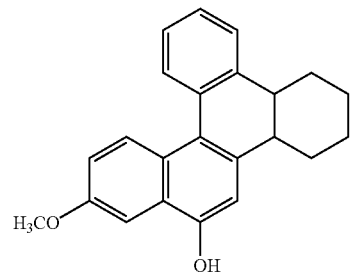

and 5.5 g (0.022 mols) of the following propargyl alcohol derivative

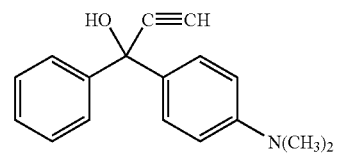

were dissolved in 50 ml of toluene, followed by the addition of 0.05 g of a p-toluenesulfonic acid, and the mixture was stirred at a refluxing temperature for one hour. After the reaction, the solvent was removed, and the reaction product was refined by chromatography on silica gel to obtain 3.9 g of a pale bluish powdery product, yield, 35%.

Elemental analysis of the product showed C, 85.23%, H, 6.62%, N, 2.51%, O, 5.73%, which were in very good agreement with the calculated values of C, 85.22%, H, 6.62%, N, 2.48%, O, 5.68% of $C_{40}H_{37}NO_2$.

A measurement of a proton nuclear magnetic resonance spectrum indicated a peak of 19H based on an alkylene group near δ 1.0 to 4.0 ppm, and a peak of 18H based on an aromatic proton and an alkene proton near δ 5.6 to 9.0 ppm (FIG. 1).

Further, a measurement of a $^{13}$C-nuclear magnetic resonance spectrum indicated a peak based on a carbon atom of an aromatic ring near δ 110 to 160 ppm, a peak based on a carbon atom of an alkene near δ 80 to 140 ppm, and a peak based on a carbon atom of an alkyl at δ 20 to 60 ppm.

From the above results, it was confirmed that the isolated product was a compound represented by the following structural formula.

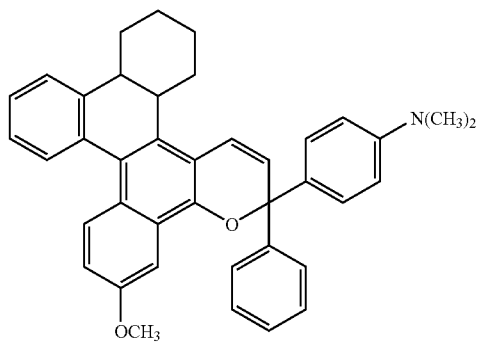

Examples 2 to 36

Chromene compounds shown in Tables 1 to 9 were synthesized in the same manner as in Example 1. The obtained products were analyzed for their structures relying on the same means for confirming structure as that of Example 1. It was confirmed that the obtained products were the compounds represented by the structural formulas shown in Tables 1 to 9. Tables 1 to 9 also show their yields.

In the structural formulas shown in Tables 1 to 9, Me represents a methyl group.

Example 37

5.8 Grams (0.02 mols) of the following naphthol derivative

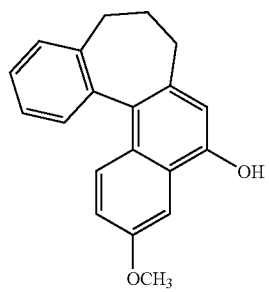

and 5.5 g (0.022 mols) of the propargyl alcohol derivative used in Example 1 were dissolved in 50 ml of toluene, followed by the addition of 0.05 g of a p-toluenesulfonic acid, and the mixture was stirred at a refluxing temperature for one hour. After the reaction, the solvent was removed, and the reaction product was refined by chromatography on silica gel to obtain 2.9 g of a pale bluish powdery product, yield, 28%.

Elemental analysis of the product showed C, 84.89%, H, 6.34%, N, 2.68%, O, 6.08%, which were in very good agreement with the calculated values of C, 84.86%, H, 6.35%, N, 2.67%, O, 6.11% of $C_{37}H_{33}NO_2$.

Figure 2:
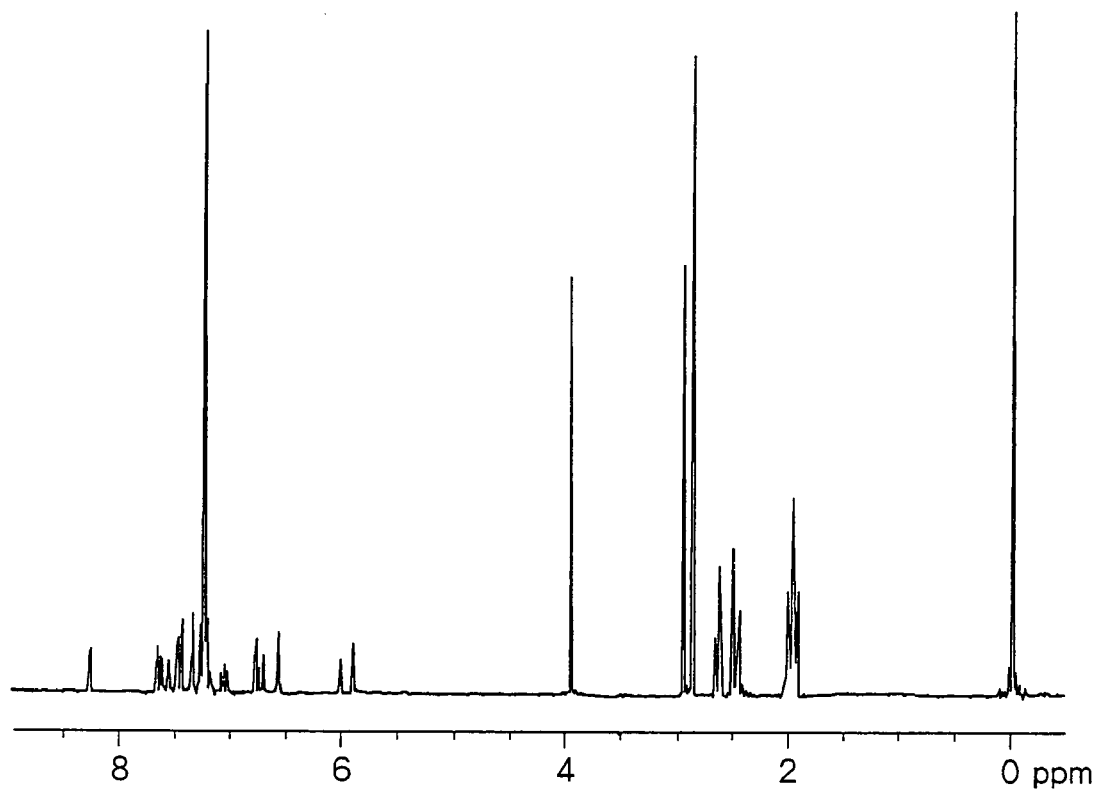

A measurement of a proton nuclear magnetic resonance spectrum indicated a peak of 15H based on an alkylene group near δ 1.0 to 4.0 ppm, and a peak of 18H based on an aromatic proton and an alkene proton near δ 5.6 to 9.0 ppm (FIG. 2).

Further, a measurement of a $^{13}$C-nuclear magnetic resonance spectrum indicated a peak based on a carbon atom of an aromatic ring near δ 110 to 160 ppm, a peak based on a carbon atom of an alkene near δ 80 to 140 ppm, and a peak based on a carbon atom of an alkyl at δ 20 to 60 ppm.

From the above results, it was confirmed that the isolated product was a compound represented by the following structural formula.

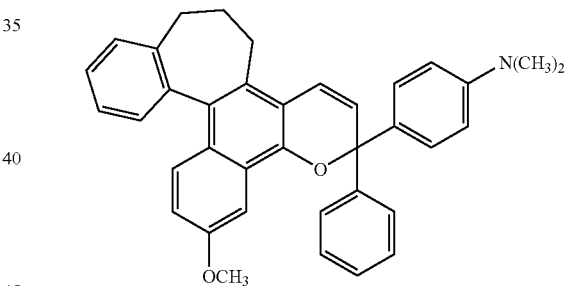

Examples 38 to 47

Chromene compounds shown in Tables 10 to 12 were synthesized in the same manner as in Example 37. The obtained products were analyzed for their structures relying on the same means for confirming structure as that of Example 1. It was confirmed that the obtained products were the compounds represented by the structural formulas shown in Tables 10 to 12. Tables 10 to 12 also show their yields.

In Tables, Me represents a methyl group and Ph represents a phenyl group.

Further, Tables 13 to 17 show values of elemental analysis of the chromene compounds synthesized in Examples 1 to 47 and values calculated from the structural formulas of the compounds.

TABLE 1

| Ex. No. | Starting material | |
|---|---|---|
| | Naphthol derivative | Propargyl alcohol |
| 1 | *[structure: methoxy-substituted hexahydrodibenzo[c,p]chrysen-ol]* | *[structure: 1-phenyl-1-(4-dimethylaminophenyl)-2-propyn-1-ol]* |
| 2 | *[structure: dimethoxy-substituted polycyclic naphthol derivative]* | *[structure: 1-phenyl-1-(4-dimethylaminophenyl)-2-propyn-1-ol]* |
| 3 | *[structure: cumyl/methoxy-substituted cyclopenta-fused chrysenol]* | *[structure: 1-phenyl-1-(4-dimethylaminophenyl)-2-propyn-1-ol]* |
| 4 | *[structure: piperidinyl-substituted hexahydrochrysenol]* | *[structure: 1-phenyl-1-(4-dimethylaminophenyl)-2-propyn-1-ol]* |

TABLE 1-continued

| Ex. No. | Product | Yield (%) |
| --- | --- | --- |
| 1 | | 35 |
| 2 | | 27 |
| 3 | | 31 |
| 4 | | 23 |

TABLE 2

| Ex. No. | Starting material | | Product | Yield (%) |
|---|---|---|---|---|
| | Naphthol derivative | Propargyl alcohol | | |
| 5 | | | | 15 |
| 6 | | | | 9 |
| 7 | | | | 19 |

TABLE 2-continued

| | Starting material | | | |
|---|---|---|---|---|
| Ex. No. | Naphthol derivative | Propargyl alcohol | Product | Yield (%) |
| 8 | [structure] | [structure] | [structure] | 8 |

TABLE 18

| Ex. No. | λmax (nm) | Color density ε(120) − ε(0) | Fading rate τ1/2 (min) | Initial color YI | Remaining ratio {(A200/A0) × 100} | Intensity ratio of color densities |
|---|---|---|---|---|---|---|
| 1 | 500 | 1.00 | 0.9 | | | |
| | 592 | 1.12 | 0.9 | 2 | 82 | 0.89 |
| 2 | 502 | 0.78 | 0.9 | | | |
| | 594 | 0.89 | 0.9 | 3 | 81 | 0.88 |
| 3 | 490 | 0.71 | 1.0 | | | |
| | 582 | 0.91 | 1.0 | 2 | 81 | 0.78 |
| 4 | 470 | 1.21 | 1.3 | | | |
| | 570 | 0.92 | 1.3 | 7 | 77 | 1.32 |
| 5 | 498 | 0.65 | 0.8 | | | |
| | 590 | 0.72 | 0.8 | 1 | 83 | 0.90 |
| 6 | 474 | 1.30 | 0.6 | | | |
| | 578 | 1.10 | 0.6 | 4 | 78 | 1.18 |
| 7 | 494 | 0.65 | 0.7 | | | |
| | 584 | 0.78 | 0.8 | 3 | 90 | 0.83 |
| 8 | 474 | 1.11 | 0.9 | | | |
| | 578 | 1.00 | 0.9 | 3 | 90 | 1.11 |
| 9 | 494 | 0.62 | 0.7 | | | |
| | 586 | 0.73 | 0.7 | 2 | 79 | 0.85 |
| 10 | 484 | 0.66 | 1.6 | | | |
| | 572 | 0.76 | 1.6 | 3 | 82 | 0.87 |

TABLE 3

| | Starting material | |
|---|---|---|
| Ex. No. | Naphthol derivative | Propargyl alcohol |
| 9 | [structure] | [structure] |

TABLE 3-continued
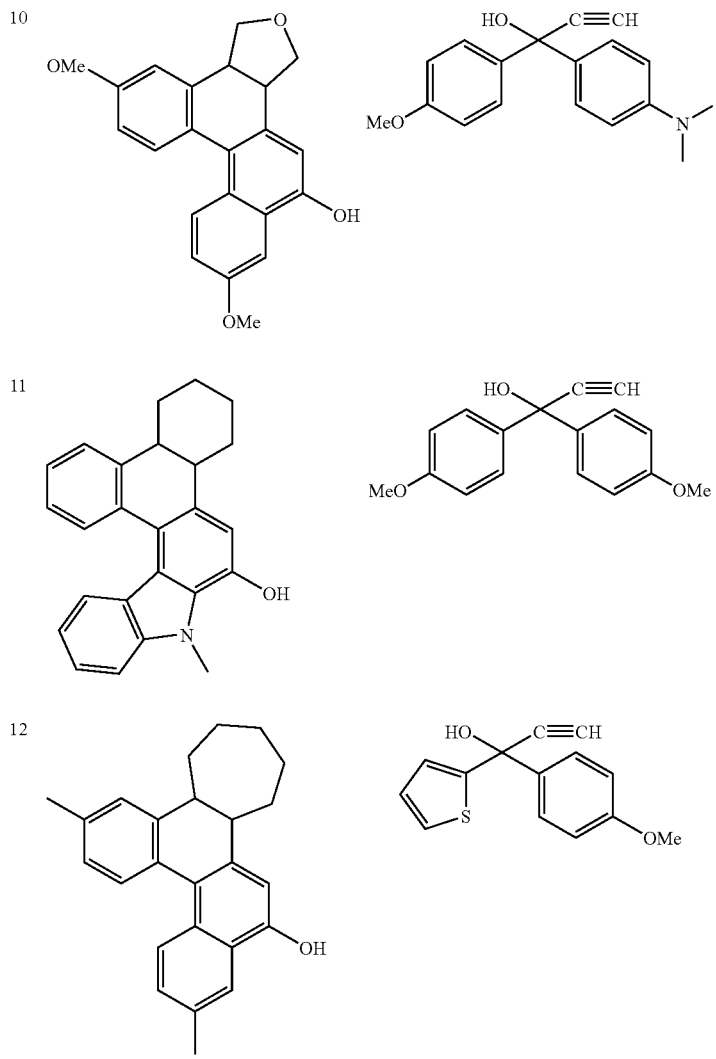
| Ex. No. | Product | Yield (%) |
|---|---|---|
| 9 | | 22 |
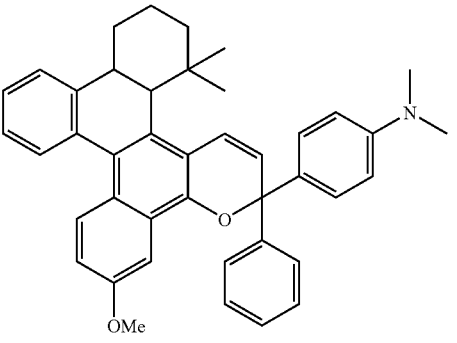

TABLE 3-continued
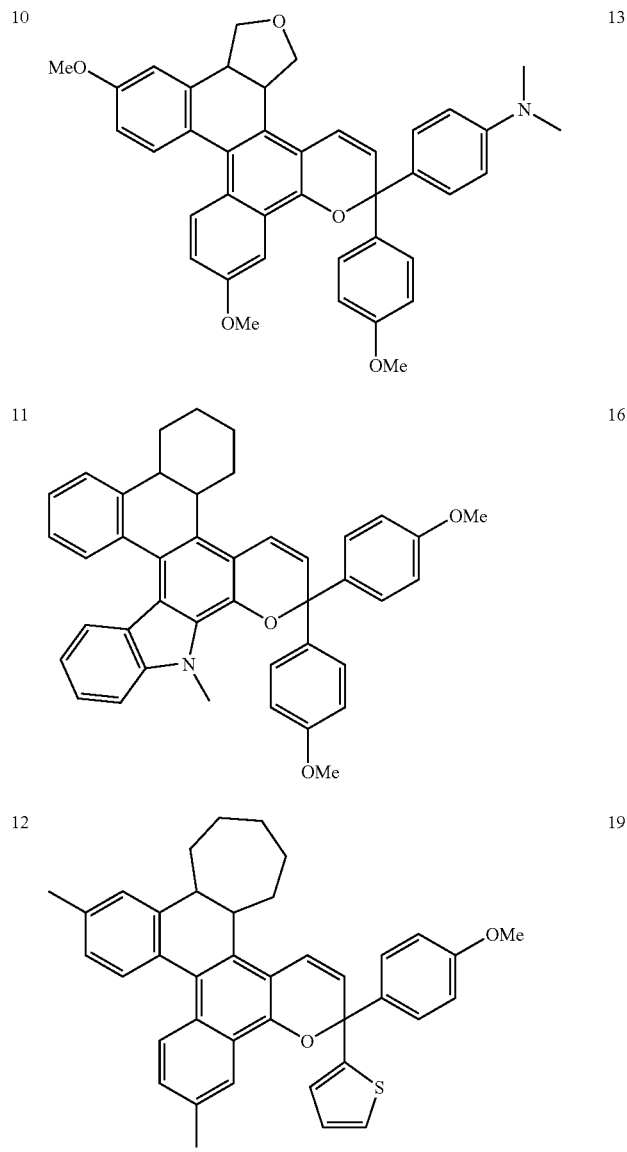
TABLE 4
| | Starting material | |
|---|---|---|
| Ex. No. | Naphthol derivative | Propargyl alcohol |
| 13 | | |

TABLE 4-continued
| 14 | |
|---|---|
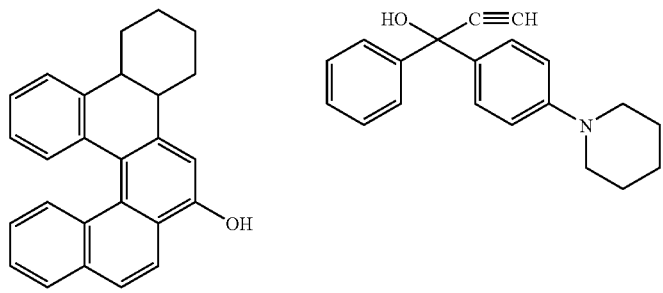
| 15 | |
|---|---|
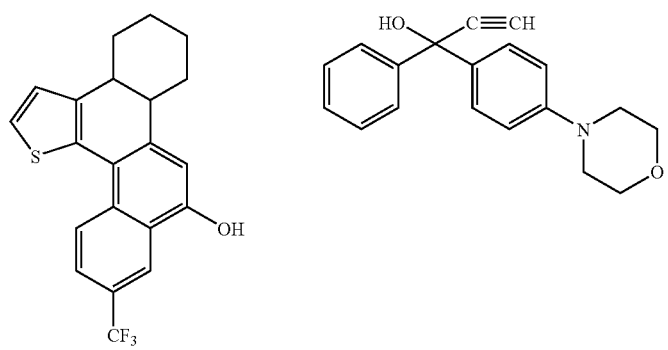
| 16 | |
|---|---|
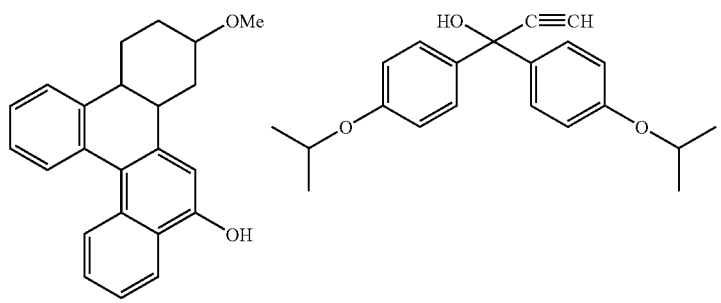
| Ex. No. | Product | Yield (%) |
|---|---|---|
| 13 | 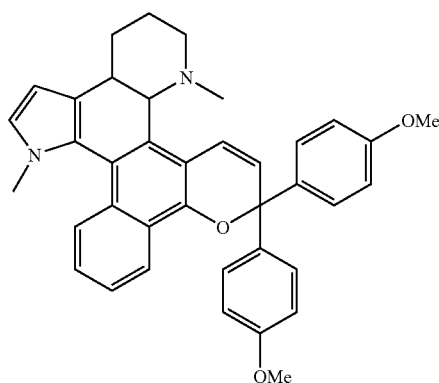 | 22 |

TABLE 4-continued
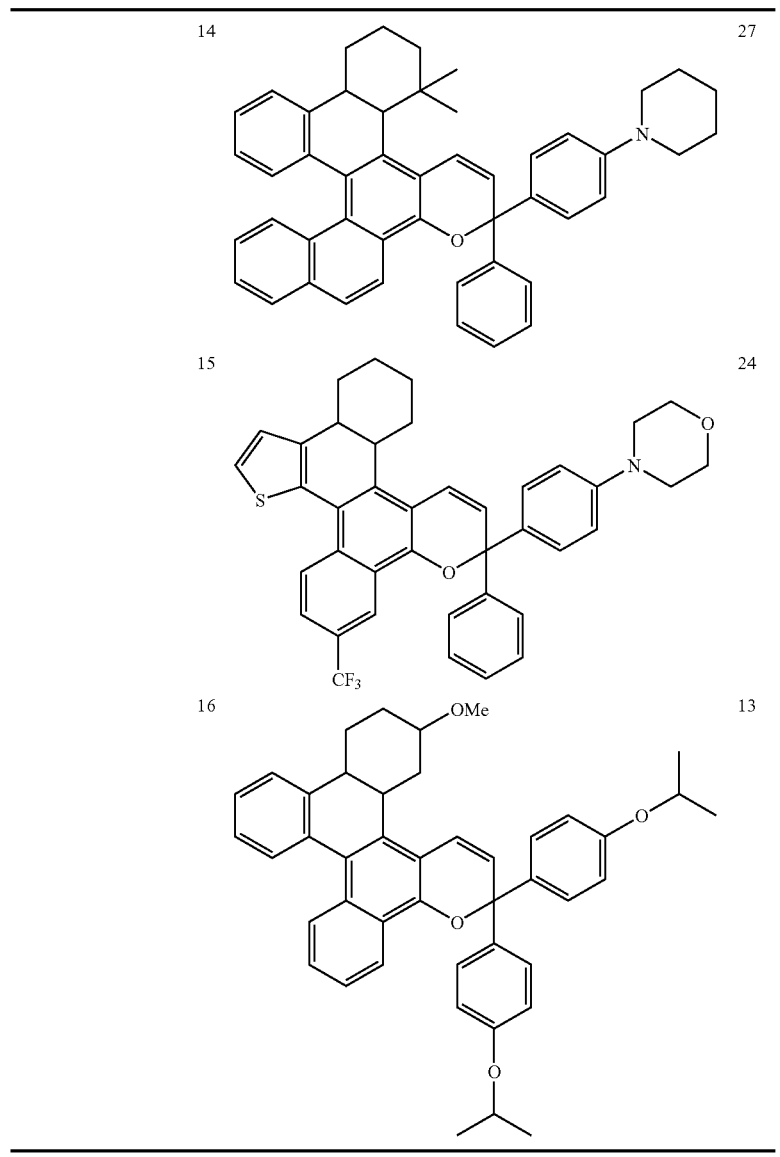
TABLE 5
| | Starting material | |
|---|---|---|
| Ex. No. | Naphthol derivative | Propargyl alcohol |
| 17 | | |
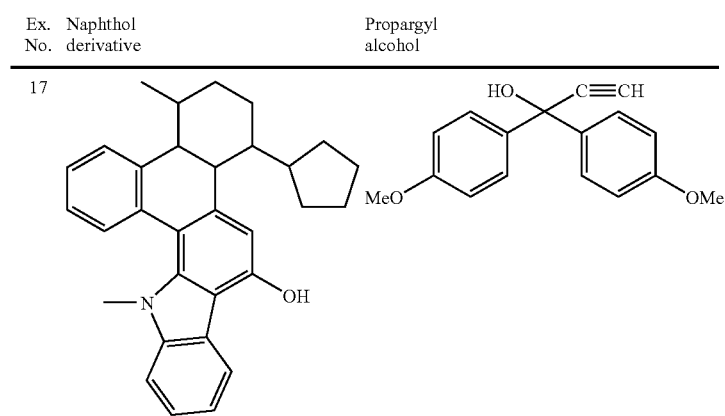

TABLE 5-continued
| 18 | 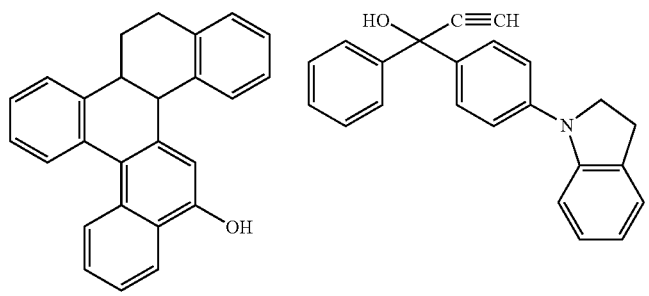 |
| 19 | 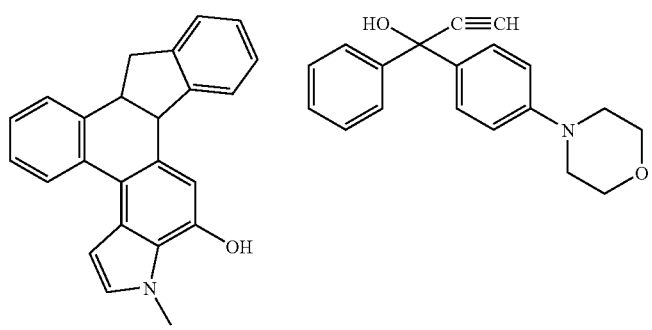 |
| 20 | 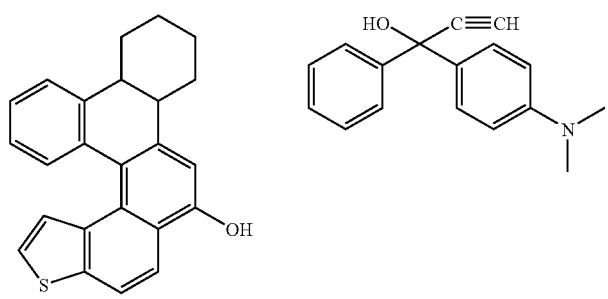 |
| Ex. No. | Product |
| --- | --- |
| 17 | 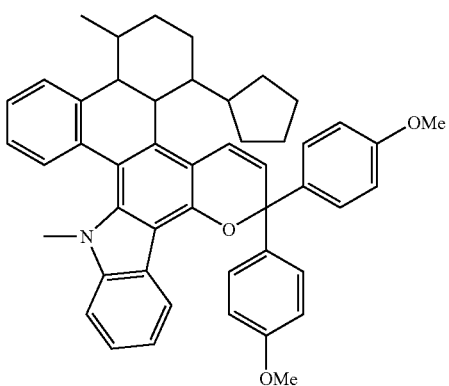 |

TABLE 5-continued
| | |
|---|---|
| 18 | 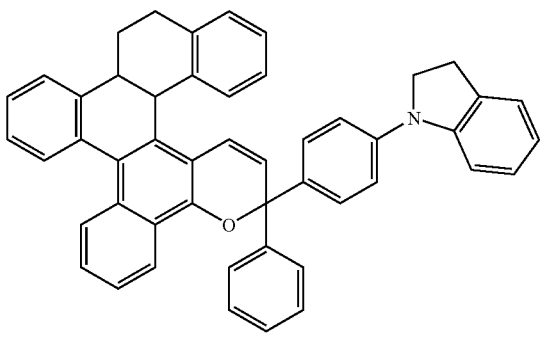 |
| 19 | 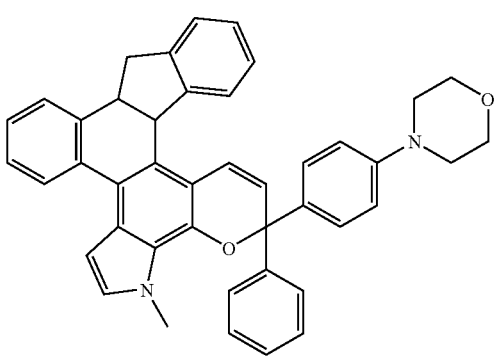 |
| 20 | 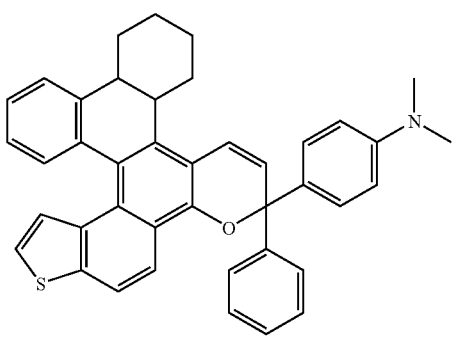 |
TABLE 6
| | Starting material | | | |
|---|---|---|---|---|
| Ex. No. | Naphthol derivative | Propargyl alcohol | Product | Yield (%) |
| 21 | | | | 26 |

TABLE 6-continued

| Ex. No. | Starting material — Naphthol derivative | Starting material — Propargyl alcohol | Product | Yield (%) |
|---|---|---|---|---|
| 22 | (structure) | (structure) | (structure) | 15 |
| 23 | (structure) | (structure) | (structure) | 18 |
| 24 | (structure) | (structure) | (structure) | 23 |

TABLE 7
| Ex. No. | Starting material | | Product | Yield (%) |
|---|---|---|---|---|
| | Naphthol derivative | Propargyl alcohol | | |
| 25 | 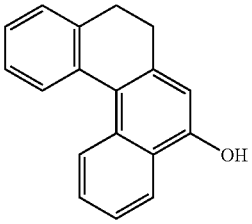 | 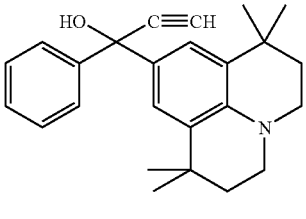 | 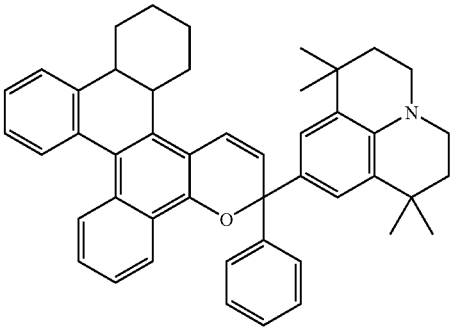 | 13 |
| 26 | 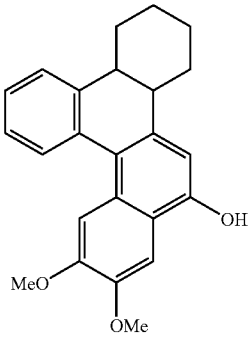 | 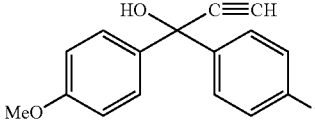 | 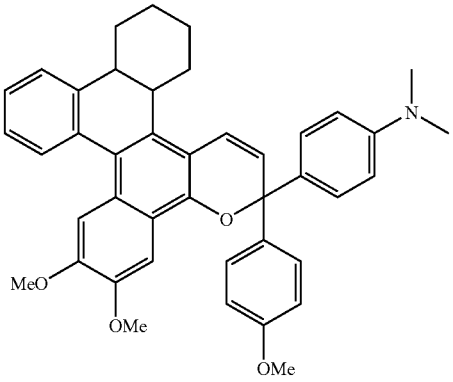 | 19 |
| 27 | 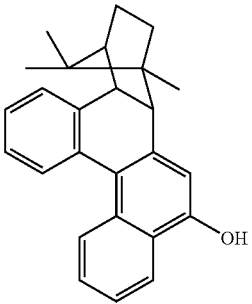 | 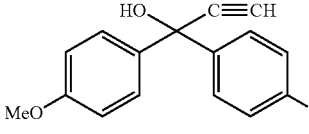 | 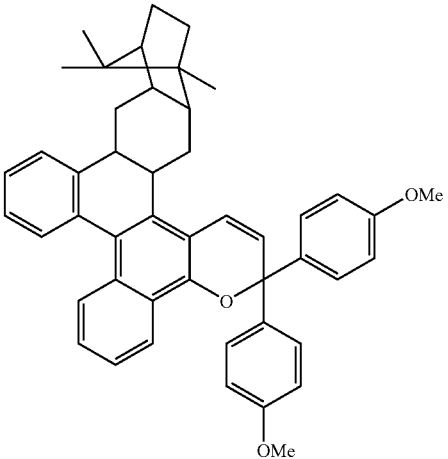 | 9 |

TABLE 7-continued
| | Starting material | | | |
|---|---|---|---|---|
| Ex. No. | Naphthol derivative | Propargyl alcohol | Product | Yield (%) |
| 28 | 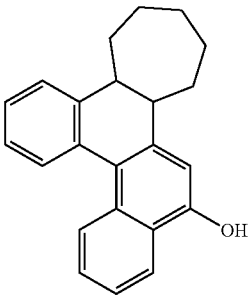 | 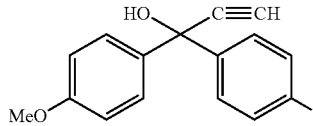 | 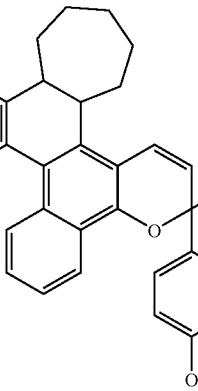 | 23 |
TABLE 8
| | Starting material | | | |
|---|---|---|---|---|
| Ex. No. | Naphthol derivative | Propargyl alcohol | Product | Yield (%) |
| 29 | 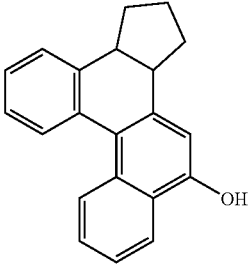 | 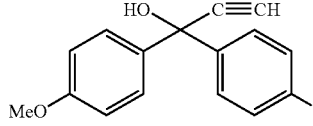 | 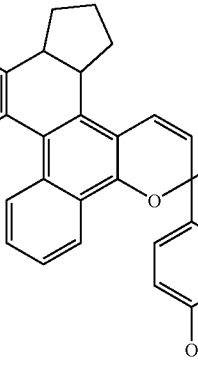 | 31 |
| 30 | 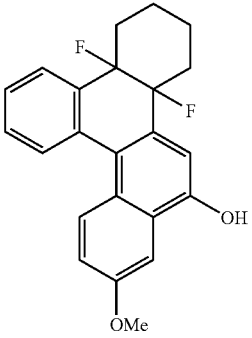 | 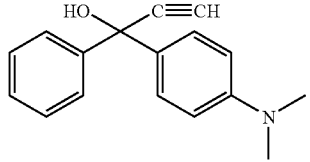 | 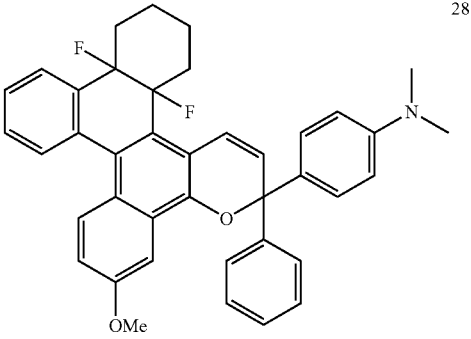 | 28 |

TABLE 8-continued

| | Starting material | | | |
|---|---|---|---|---|
| Ex. No. | Naphthol derivative | Propargyl alcohol | Product | Yield (%) |
| 31 | | | | 14 |
| 32 | | | | 15 |

TABLE 9

| | Starting material | | | |
|---|---|---|---|---|
| Ex. No. | Naphthol derivative | Propargyl alcohol | Product | Yield (%) |
| 33 | | | | 17 |

TABLE 9-continued

| Ex. No. | Starting material | | Product | Yield (%) |
| --- | --- | --- | --- | --- |
| | Naphthol derivative | Propargyl alcohol | | |
| 34 | | | | 16 |
| 35 | | | | 21 |
| 36 | | | | 20 |

TABLE 10

| Ex. No. | Starting material | |
|---|---|---|
| | Naphthol derivative | Propargyl alcohol |
| 37 | | |
| 38 | | |
| 39 | | |
| 40 | | |

TABLE 10-continued
| Ex. No. | Product | Yield (%) |
|---|---|---|
| 37 | 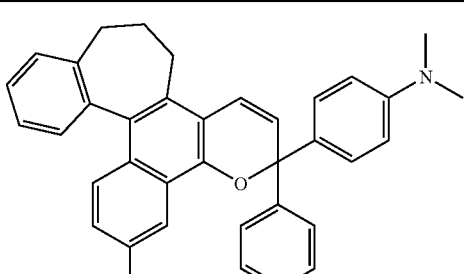 | 28 |
| 38 | 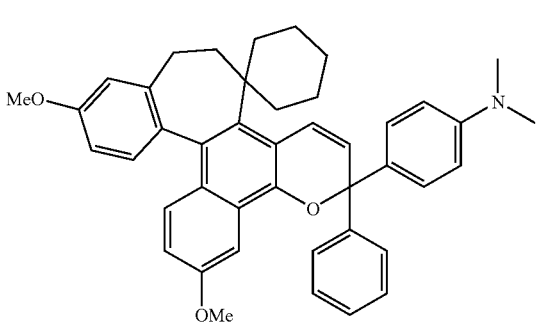 | 18 |
| 39 | 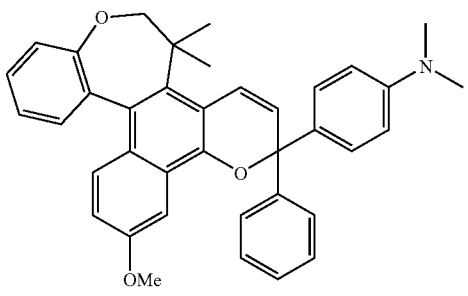 | 20 |
| 40 | 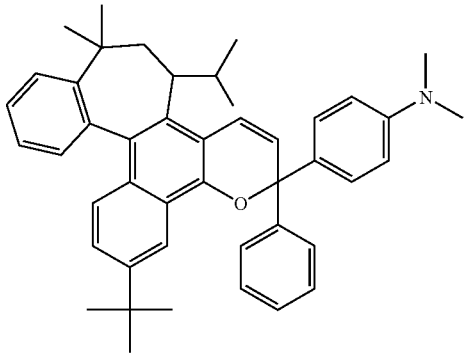 | 12 |

TABLE 11
| Ex. No. | Starting material | |
|---|---|---|
| | Naphthol derivative | Propargyl alcohol |
| 41 | 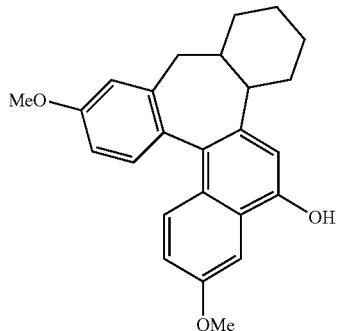 | 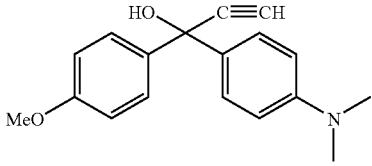 |
| 42 | 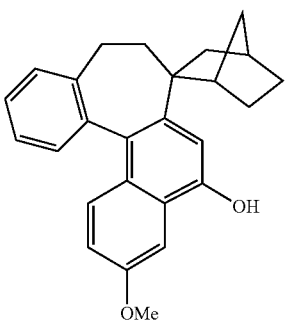 | 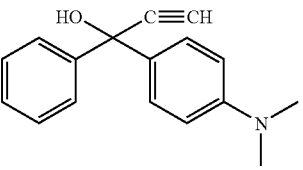 |
| 43 | 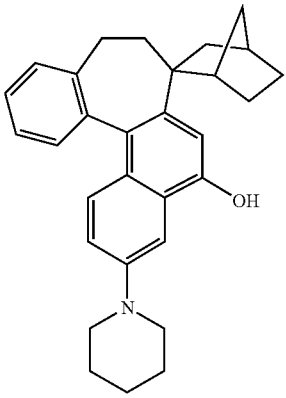 | 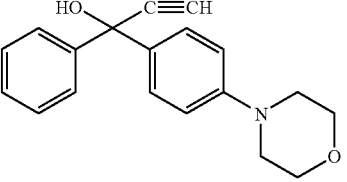 |
| 44 | 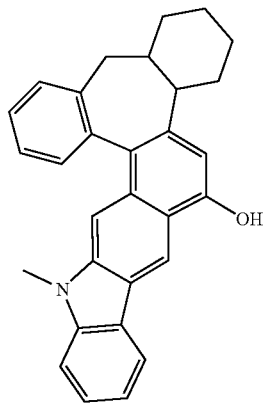 | 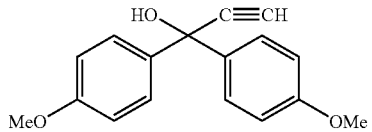 |

TABLE 11-continued

| Ex. No. | Product | Yield (%) |
|---|---|---|
| 41 | | 23 |
| 42 | | 16 |
| 43 | | 15 |
| 44 | | 12 |

TABLE 12

| Ex. No. | Starting material | | Product | Yield (%) |
|---|---|---|---|---|
| | Naphthol derivative | Propargyl alcohol | | |
| 45 | (structure) | (structure) | (structure) | 9 |
| 46 | (structure) | (structure) | (structure) | 15 |
| 47 | (structure) | (structure) | (structure) | 16 |

TABLE 13

| Ex. No. | Found | | | | | Calculated | | | | | 1H-NMR (NMR) |
|---|---|---|---|---|---|---|---|---|---|---|---|
| | C | H | N | O | others | C | H | N | O | others | |
| 1 | 85.23 | 6.62 | 2.51 | 5.73 | | 85.22 | 6.62 | 2.48 | 5.68 | | δ5.6~9.0 18H<br>δ1.0~4.0 19H |
| 2 | 83.43 | 7.03 | 2.14 | 7.41 | | 83.43 | 7.00 | 2.16 | 7.41 | | δ5.6~9.0 18H<br>δ1.0~4.0 27H |
| 3 | 86.34 | 6.75 | 2.11 | 4.80 | | 86.32 | 6.79 | 2.10 | 4.79 | | δ5.6~9.0 22H<br>δ1.0~4.0 23H |
| 4 | 85.66 | 7.18 | 4.56 | 2.60 | | 85.67 | 7.19 | 4.54 | 2.59 | | δ5.6~9.0 18H<br>δ1.0~4.0 23H |
| 5 | 85.28 | 7.46 | 2.21 | 5.07 | | 85.27 | 7.47 | 2.21 | 5.05 | | δ5.6~9.0 18H<br>δ1.0~4.0 26H |
| 6 | 83.88 | 7.04 | 4.26 | 4.85 | | 83.85 | 7.04 | 4.25 | 4.86 | | δ5.6~9.0 18H<br>δ1.0~4.0 41H |
| 7 | 85.21 | 6.99 | 2.39 | 5.46 | | 85.24 | 6.98 | 2.37 | 5.46 | | δ5.6~9.0 18H<br>δ1.0~4.0 23H |
| 8 | 83.96 | 7.48 | 4.00 | 4.57 | | 83.97 | 7.46 | 4.02 | 4.58 | | δ5.6~9.0 17H<br>δ1.0~4.0 35H<br>δ5.6~9.0 18H |

TABLE 13-continued

| Ex. No. | Elemental analysis | | | | | | | | | | 1H-NMR (NMR) | |
|---|---|---|---|---|---|---|---|---|---|---|---|---|
| | Found | | | | | Calculated | | | | | | |
| | C | H | N | O | others | C | H | N | O | others | | |
| 9 | 85.21 | 6.99 | 2.39 | 5.41 | | 85.23 | 7.01 | 2.38 | 5.44 | | δ1.0~4.0 | 23H |
| | | | | | | | | | | | δ5.6~9.0 | 16H |
| 10 | 78.55 | 6.11 | 2.29 | 13.05 | | 78.54 | 6.10 | 2.29 | 13.08 | | δ1.0~4.0 | 21H |

TABLE 14

| Ex. No. | Elemental analysis | | | | | | | | | | 1H-NMR (NMR) | |
|---|---|---|---|---|---|---|---|---|---|---|---|---|
| | Found | | | | | Calculated | | | | | | |
| | C | H | N | O | others | C | H | N | O | others | | |
| 11 | 83.57 | 6.17 | 2.34 | 7.92 | | 83.55 | 6.18 | 2.32 | 7.95 | | δ5.6~9.0 | 18H |
| | | | | | | | | | | | δ1.0~4.0 | 19H |
| 12 | 82.43 | 6.59 | 5.50 | 5.48 | | 82.44 | 6.57 | 5.49 | 5.50 | | δ5.6~9.0 | 15H |
| | | | | | | | | | | | δ1.0~4.0 | 23H |
| 13 | 80.25 | 6.36 | 4.92 | 8.47 | | 80.25 | 6.38 | 4.93 | 8.44 | | δ5.6~9.0 | 16H |
| | | | | | | | | | | | δ1.0~4.0 | 20H |
| 14 | 88.59 | 6.61 | 2.27 | 2.53 | | 88.57 | 6.62 | 2.25 | 2.56 | | δ5.6~9.0 | 21H |
| | | | | | F: 8.76 | | | | | F: 8.77 | δ1.0~4.0 | 20H |
| 15 | 73.95 | 5.27 | 2.18 | 4.90 | S: 4.94 | 73.94 | 5.27 | 2.16 | 4.91 | S: 4.94 | δ5.6~9.0 | 16H |
| | | | | | | | | | | | δ1.0~4.0 | 18H |
| 16 | 82.98 | 6.95 | | 10.07 | | 82.99 | 6.96 | | 10.05 | | δ5.6~9.0 | 18H |
| | | | | | | | | | | | δ1.0~4.0 | 26H |
| 17 | 84.04 | 6.93 | 2.05 | 6.98 | | 84.05 | 6.91 | 2.04 | 7.00 | | δ5.6~9.0 | 18H |
| | | | | | | | | | | | δ1.0~4.0 | 29H |
| 18 | 89.75 | 5.70 | 2.13 | 2.42 | | 89.74 | 5.69 | 2.14 | 2.44 | | δ5.6~9.0 | 27H |
| | | | | | | | | | | | δ1.0~4.0 | 10H |
| 19 | 84.30 | 5.91 | 4.59 | 5.19 | | 84.28 | 5.92 | 4.57 | 5.22 | | δ5.6~9.0 | 21H |
| | | | | | | | | | | | δ1.0~4.0 | 15H |
| 20 | 83.48 | 6.00 | 2.38 | 2.69 | S: 5.45 | 83.49 | 5.98 | 2.37 | 2.71 | S: 5.44 | δ5.6~9.0 | 19H |
| | | | | | | | | | | | δ1.0~4.0 | 16H |

TABLE 15

| Ex. No. | Elemental analysis | | | | | | | | | | 1H-NMR (NMR) | |
|---|---|---|---|---|---|---|---|---|---|---|---|---|
| | Found | | | | | Calculated | | | | | | |
| | C | H | N | O | others | C | H | N | O | others | | |
| 21 | 85.85 | 6.16 | 2.43 | 5.60 | | 85.83 | 6.15 | 2.44 | 5.58 | | δ5.6~9.0 | 19H |
| | | | | | | | | | | | δ1.0~4.0 | 16H |
| 22 | 87.74 | 7.38 | 2.27 | 2.60 | | 87.76 | 7.37 | 2.27 | 2.60 | | δ5.6~9.0 | 19H |
| | | | | | | | | | | | δ1.0~4.0 | 26H |
| 23 | 78.38 | 5.92 | 2.36 | 8.00 | S: 5.34 | 78.36 | 5.90 | 2.34 | 8.03 | S: 5.36 | δ5.6~9.0 | 17H |
| | | | | | | | | | | | δ1.0~4.0 | 18H |
| 24 | 83.97 | 6.60 | 2.14 | 7.30 | | 83.99 | 6.59 | 2.13 | 7.30 | | δ5.6~9.0 | 20H |
| | | | | | | | | | | | δ1.0~4.0 | 23H |
| 25 | 87.93 | 7.40 | 2.19 | 2.47 | | 87.94 | 7.38 | 2.18 | 2.49 | | δ5.6~9.0 | 17H |
| | | | | | | | | | | | δ1.0~4.0 | 30H |
| 26 | 80.87 | 6.61 | 2.26 | 10.29 | | 80.87 | 6.63 | 2.25 | 10.26 | | δ5.6~9.0 | 16H |
| | | | | | | | | | | | δ1.0~4.0 | 25H |
| 27 | 85.39 | 6.65 | | 7.94 | | 85.40 | 6.67 | | 7.94 | | δ5.6~9.0 | 18H |
| | | | | | | | | | | | δ1.0~4.0 | 22H |
| 28 | 85.11 | 6.62 | | 8.27 | | 85.09 | 6.62 | | 8.29 | | δ5.6~9.0 | 18H |
| | | | | | | | | | | | δ1.0~4.0 | 20H |
| 29 | 85.06 | 6.02 | | 8.92 | | 85.05 | 6.01 | | 8.94 | | δ5.6~9.0 | 18H |
| | | | | | | | | | | | δ1.0~4.0 | 14H |
| 30 | 80.10 | 5.90 | 2.35 | 5.32 | F: 6.33 | 80.11 | 5.88 | 2.34 | 5.34 | F: 6.34 | δ5.6~9.0 | 18H |
| | | | | | | | | | | | δ1.0~4.0 | 19H |

TABLE 16

| Ex. No. | Elemental analysis | | | | | | | | | | 1H-NMR (NMR) | |
|---|---|---|---|---|---|---|---|---|---|---|---|---|
| | Found | | | | | Calculated | | | | | | |
| | C | H | N | O | others | C | H | N | O | others | | |
| 31 | 84.41 | 6.08 | 6.89 | 2.62 | | 84.42 | 6.10 | 6.87 | 2.62 | | δ5.6~9.0<br>δ1.0~4.0 | 18H<br>19H |
| 32 | 83.57 | 6.19 | 2.31 | 7.97 | | 83.55 | 6.18 | 2.32 | 7.95 | | δ5.6~9.0<br>δ1.0~4.0 | 18H<br>19H |
| 33 | 81.15 | 5.67 | | 7.89 | S: 5.29 | 81.16 | 5.65 | | 7.91 | S: 5.28 | δ5.6~9.0<br>δ1.0~4.0 | 18H<br>16H |
| 34 | 81.16 | 5.66 | | 7.90 | S: 5.28 | 81.16 | 5.65 | | 7.91 | S: 5.28 | δ5.6~9.0<br>δ1.0~4.0 | 18H<br>16H |
| 35 | 83.36 | 5.82 | | 10.82 | | 83.36 | 5.80 | | 10.83 | | δ5.6~9.0<br>δ1.0~4.0 | 18H<br>16H |
| 36 | 83.37 | 5.81 | | 10.82 | | 83.36 | 5.80 | | 10.83 | | δ5.6~9.0<br>δ1.0~4.0 | 18H<br>16H |
| 37 | 84.88 | 6.34 | 2.69 | 6.08 | | 84.86 | 6.35 | 2.67 | 6.11 | | δ5.6~9.0<br>δ1.0~4.0 | 18H<br>15H |
| 38 | 83.05 | 6.95 | 2.27 | 7.72 | | 83.06 | 6.97 | 2.25 | 7.72 | | δ5.6~9.0<br>δ1.0~4.0 | 17H<br>26H |
| 39 | 82.43 | 6.35 | 2.52 | 8.70 | | 82.43 | 6.37 | 2.53 | 8.67 | | δ5.6~9.0<br>δ1.0~4.0 | 18H<br>17H |
| 40 | 88.05 | 7.56 | 2.06 | 2.33 | | 88.06 | 7.54 | 2.05 | 2.35 | | δ5.6~9.0<br>δ1.0~4.0 | 23H<br>28H |

TABLE 17

| Ex. No. | Elemental analysis | | | | | | | | | | 1H-NMR (NMR) | |
|---|---|---|---|---|---|---|---|---|---|---|---|---|
| | Found | | | | | Calculated | | | | | | |
| | C | H | N | O | others | C | H | N | O | others | | |
| 41 | 80.92 | 6.82 | 2.25 | 10.01 | | 80.97 | 6.80 | 2.20 | 10.03 | | δ5.6~9.0<br>δ1.0~4.0 | 16H<br>27H |
| 42 | 85.56 | 6.84 | 2.36 | 5.24 | | 85.54 | 6.84 | 2.32 | 5.30 | | δ5.6~9.0<br>δ1.0~4.0 | 18H<br>23H |
| 43 | 84.21 | 7.25 | 4.02 | 4.52 | | 84.20 | 7.21 | 4.01 | 4.58 | | δ5.6~9.0<br>δ1.0~4.0 | 18H<br>32H |
| 44 | 84.52 | 6.21 | 2.11 | 7.17 | | 84.53 | 6.19 | 2.10 | 7.19 | | δ5.6~9.0<br>δ1.0~4.0 | 20H<br>21H |
| 45 | 82.69 | 6.21 | 4.09 | 7.05 | | 82.67 | 6.20 | 4.10 | 7.03 | | δ5.6~9.0<br>δ1.0~4.0 | 20H<br>22H |
| 46 | 81.85 | 6.32 | | 5.92 | S: 5.91 | 81.88 | 6.31 | | 5.90 | S: 5.91 | δ5.6~9.0<br>δ1.0~4.0 | 17H<br>17H |
| 47 | 86.14 | 6.01 | 2.41 | 5.44 | | 86.12 | 6.02 | 2.39 | 5.46 | | δ5.6~9.0<br>δ1.0~4.0 | 21H<br>14H |

Applied Example

Chromene compounds obtained in Examples 1 to 47 were used to prepare mixed solutions of the chromene compounds having the following recipe.

| | |
|---|---|
| Chromene compound obtained in Example | 0.04 pts by wt |
| Tetraethylene glycol dimethacrylate | 13 pts by wt |
| 2,2-Bis[4-(methacryloxyethoxy)phenyl]propane | 48 pts by wt |
| Polyethylene glycol monoaryl ether | 2 pts by wt |
| Trimethylolpropane trimethacrylate | 20 pts by wt |
| Glycidyl methacrylate | 9 pts by wt |
| t-Butylperoxy-2-ethyl hexanate (polymerization initiator) | 1 pt by wt |

The mixed solution was poured into a mold constituted by glass plates and a gasket of an ethylene/vinyl acetate copolymer to conduct the mold polymerization. The polymerization was conducted by using an air furnace by gradually raising the temperature from 30° C. to 90° C. over 18 hours, and the temperature was maintained at 90° C. for 2 hours. After the polymerization, the polymer was removed from the glass mold.

The obtained polymer (2 mm thick) was used as a sample and was irradiated with light by using a xenon lamp L-2480 (300W) SHL-100 manufactured by Hamamatsu Photonics Co. through an aeromass filter (manufactured by Coning Co.) to develop color and to measure the photochromic properties.

The light irradiation conditions were as follows:

Temperature of sample: 20° C.±1° C.

Beam intensities on the surface of the polymer:

2.4 mW/cm$^2$ (365 nm)

24 μW/cm$^2$ (245 nm)

Light irradiation time: 120 sec.

The photochromic properties were evaluated in a manner as described below, and the results were as shown in Tables 18 to 22.

① Maximum Absorption Wavelength (λmax):

A maximum absorption wavelength after the development of color as found by using a spectrophotometer (instantaneous multi-channel photodetector MCPD 1000) manufactured by Otsuka Denshi Co. The maximum absorption wavelength is related to the color tone at the time when the color is developed.

② Color Density (Color-Developing Density){ε(120)−ε(0)}:

A difference between an absorbency {ε(120)} after irradiated with light for 120 seconds at the maximum absorption wavelength and an absorbency ε(0) in a state of not being irradiated with light. It can be said that the higher this value, the more excellent the photochromic properties are.

③ Fading Rate [$t_{1/2}$ (min)]:

The time until the absorbency of a sample at the maximum wavelength drops down to one-half the {ε(120)−ε(0)} from when the sample is no longer irradiated with light after it was irradiated with light for 120 seconds. It can be said that the shorter this time, the more excellent the photochromic properties are.

④ Initial Color (YI):

The coloring degree was measured by using a color-difference meter (SM-4) manufactured by Suga Shikenki Co. The smaller the value YI, the weaker the color in a state of not being irradiated with light, which can be said to be excellent.

⑤ Remaining Ratio (%):

The following deterioration promotion testing was conducted in order to evaluate the light resistance of color against the irradiation with light. That is, the obtained polymer (sample) was deteriorated for 200 hours by using a xenon weather meter X25 manufactured by Suga Shikenki Co. The densities of color were evaluated before and after the testing; i.e., the color density ($A_0$) was measured before the testing and the color density ($A_{200}$) was measured after the testing, and a remaining ratio (%) was calculated according to the following formula and was used as an index of light resistance of color.

Remaining ratio (%)=($A_{200}/A_0$)×100

The higher the remaining ratio, the higher the light resistance of color.

⑥ Intensity Ratio of Color Densities:

The ratio of absorbency at the maximum absorption wavelength was calculated from the following formula and was used as an index of color tone of neutral tint.

{ε1(120)−ε1(0)}/{ε2(120)−ε2(0)}

ε1: absorbency at the maximum absorption wavelength on the short wavelength side,
ε2: absorbency at the maximum absorption wavelength on the long wavelength side.

A favorable neutral tint is obtained as the intensity ratio approaches 1.

For comparison, photochromic polymers were obtained in the same manner by using the compounds represented by the formulas (A), (B) and (C) of prior art to evaluate their properties (Comparative Examples 1 to 3). The results were as shown in Table 23.

From the experimental results shown in Tables 18 to 23, it will be understood that the chromene compounds of the present invention obtained in Examples 1 to 47 are superior to those of Comparative Examples 1 to 3 with respect to three effects, i.e., color fading rate, initial color and intensity ratio of color densities.

TABLE 19

| Ex. No. | λmax (nm) | Color density ε(120) − ε(0) | Fading rate τ1/2 (min) | Initial color YI | Remaining ratio {(A200/A0) × 100} | Intensity ratio of color densities |
|---|---|---|---|---|---|---|
| 11 | 468 | 1.28 | 0.8 | | | |
|  | 588 | 0.87 | 0.8 | 6 | 80 | 1.47 |
| 12 | 466 | 1.15 | 1.0 | | | |
|  | 578 | 1.12 | 1.0 | 6 | 76 | 1.03 |
| 13 | 468 | 0.78 | 1.1 | | | |
|  | 576 | 0.82 | 1.1 | 5 | 81 | 0.95 |
| 14 | 492 | 0.79 | 1.1 | | | |
|  | 586 | 0.92 | 1.1 | 2 | 83 | 0.86 |
| 15 | 476 | 0.82 | 1.2 | | | |
|  | 582 | 0.84 | 1.2 | 3 | 78 | 0.98 |
| 16 | 488 | 0.86 | 0.7 | | | |
|  | 586 | 0.90 | 0.7 | 3 | 81 | 0.96 |
| 17 | 468 | 1.15 | 0.8 | | | |
|  | 588 | 0.83 | 0.8 | 6 | 79 | 1.39 |
| 18 | 496 | 0.80 | 0.7 | | | |
|  | 590 | 0.92 | 0.7 | 5 | 80 | 0.87 |
| 19 | 466 | 1.09 | 0.9 | | | |
|  | 580 | 0.78 | 0.9 | 7 | 81 | 1.40 |
| 20 | 498 | 0.99 | 1.0 | | | |
|  | 596 | 1.15 | 1.0 | 5 | 77 | 0.86 |

TABLE 20

| Ex. No. | λmax (nm) | Color density ε(120) − ε(0) | Fading rate τ1/2 (min) | Initial color YI | Remaining ratio {(A200/A0) × 100} | Intensity ratio of color densities |
|---|---|---|---|---|---|---|
| 21 | 498 | 0.97 | 1.0 | | | |
|  | 596 | 1.12 | 1.0 | 4 | 81 | 0.87 |
| 22 | 490 | 0.76 | 0.6 | | | |
|  | 588 | 0.86 | 0.6 | 1 | 82 | 0.88 |
| 23 | 500 | 0.72 | 1.1 | | | |
|  | 606 | 0.88 | 1.1 | 2 | 80 | 0.82 |
| 24 | 500 | 0.68 | 0.7 | | | |
|  | 602 | 0.82 | 0.7 | 4 | 79 | 0.83 |
| 25 | 492 | 0.64 | 0.6 | | | |
|  | 600 | 0.79 | 0.6 | 2 | 76 | 0.81 |
| 26 | 500 | 0.76 | 1.0 | | | |
|  | 612 | 0.90 | 1.0 | 4 | 80 | 0.84 |
| 27 | 466 | 0.81 | 0.7 | | | |
|  | 572 | 0.93 | 0.7 | 2 | 84 | 0.87 |
| 28 | 466 | 1.02 | 1.1 | | | |
|  | 572 | 1.19 | 1.1 | 2 | 84 | 0.86 |
| 29 | 466 | 1.15 | 1.2 | | | |
|  | 574 | 1.32 | 1.2 | 2 | 85 | 0.87 |
| 30 | 498 | 0.96 | 0.9 | | | |
|  | 592 | 1.08 | 0.9 | 1 | 83 | 0.89 |

TABLE 21

| Ex. No. | λmax (nm) | Color density ε(120) − ε(0) | Fading rate τ1/2 (min) | Initial color YI | Remaining ratio {(A200/A0) × 100} | Intensity ratio of color densities |
|---|---|---|---|---|---|---|
| 31 | 478 | 1.20 | 0.7 | | | |
|  | 582 | 0.93 | 0.7 | 7 | 81 | 1.29 |
| 32 | 468 | 1.25 | 1.1 | | | |
|  | 576 | 0.91 | 1.1 | 7 | 80 | 1.37 |
| 33 | 468 | 1.31 | 1.2 | | | |
|  | 584 | 0.97 | 1.2 | 7 | 76 | 1.35 |
| 34 | 466 | 1.21 | 1.3 | | | |
|  | 584 | 1.01 | 1.3 | 7 | 76 | 1.20 |
| 35 | 468 | 1.29 | 1.1 | | | |

TABLE 21-continued

| Ex. No. | λmax (nm) | Color density ε(120) − ε(0) | Fading rate τ1/2 (min) | Initial color YI | Remaining ratio {(A200/A0) × 100} | Intensity ratio of color densities |
|---|---|---|---|---|---|---|
|  | 586 | 0.96 | 1.1 | 6 | 80 | 1.34 |
| 36 | 468 | 1.19 | 1.1 |  |  |  |
|  | 584 | 0.93 | 1.1 | 6 | 81 | 1.27 |
| 37 | 488 | 0.66 | 0.6 |  |  |  |
|  | 586 | 0.79 | 0.6 | 2 | 86 | 0.84 |
| 38 | 490 | 0.58 | 0.5 |  |  |  |
|  | 596 | 0.61 | 0.5 | 4 | 85 | 0.95 |
| 39 | 484 | 0.72 | 0.5 |  |  |  |
|  | 582 | 0.86 | 0.5 | 3 | 83 | 0.84 |
| 40 | 494 | 0.92 | 0.9 |  |  |  |
|  | 600 | 1.05 | 0.9 | 6 | 85 | 0.88 |

TABLE 22

| Ex. No. | λmax (nm) | Color density ε(120) − ε(0) | Fading rate τ1/2 (min) | Initial color YI | Remaining ratio {(A200/A0) × 100} | Intensity ratio of color densities |
|---|---|---|---|---|---|---|
| 41 | 500 | 0.86 | 0.5 |  |  |  |
|  | 612 | 0.93 | 0.5 | 5 | 86 | 0.92 |
| 42 | 488 | 0.64 | 0.5 |  |  |  |
|  | 586 | 0.72 | 0.5 | 3 | 87 | 0.89 |
| 43 | 498 | 1.12 | 1.3 |  |  |  |
|  | 608 | 0.98 | 1.3 | 8 | 80 | 1.14 |
| 44 | 486 | 1.29 | 1.2 |  |  |  |
|  | 592 | 0.92 | 1.2 | 9 | 81 | 1.40 |
| 45 | 488 | 1.32 | 0.6 |  |  |  |
|  | 598 | 0.88 | 0.6 | 9 | 81 | 1.50 |
| 46 | 478 | 1.10 | 1.0 |  |  |  |
|  | 586 | 1.12 | 1.0 | 4 | 78 | 0.98 |
| 47 | 498 | 1.15 | 0.9 |  |  |  |
|  | 604 | 1.12 | 0.8 | 6 | 81 | 1.03 |

TABLE 23

| Comp. Ex. No. | Compound No. | λmax (nm) | Color density ε(120) − ε(0) | Fading rate τ1/2 (min) | Color degree YI | Remaining ratio {(A200/A0) × 100} | Intensity ratio of color densities |
|---|---|---|---|---|---|---|---|
| 1 | A | 522 | 0.86 | 8.3 | 3 | 68 | — |
| 2 |  | 498 | 0.92 | 4.1 |  |  |  |
|  | B | 596 | 0.84 | 4.1 | 4 | 71 | 1.10 |
| 3 |  | 484 | 0.45 | 1.3 |  |  |  |
|  | C | 610 | 0.90 | 1.3 | 14 | 77 | 0.50 |

The invention claimed is:

1. A chromene compound represented by the following general formula (1),

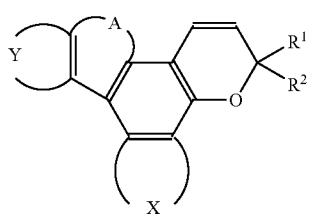

(1)

wherein R¹ and R² are, independently from each other, alkyl groups, aryl groups which may have a substituent, or heteroaryl groups which may have a substituent, and R¹ and R² together may constitute a ring;

the ring X and the ring Y represented by,

(1a)

and

(1b)

are, independently from each other, aromatic hydrocarbon rings or aromatic heterocyclic rings which may have a substituent; and the divalent bridge group A is represented by the following formula (1c-1) or (1c-2),

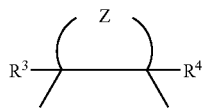

(1c-1)

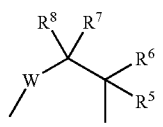

(1c-2)

wherein in the formula (1c-1), the Z represented by,

is an alicyclic hydrocarbon ring or a heterocyclic ring, which may have a substituent, R³ and R⁴ are, independently from each other, hydrogen atoms, hydroxyl groups, alkyl groups, alkoxy groups, aralkyl groups, aralkoxy groups, amino groups, substituted amino groups, cyano groups, nitro groups, halogen atoms, halogenoalkyl groups, halogenoalkoxy groups or substituted or unsubstituted alicyclic hydrocarbon groups, and in the above formula (1c-2), R⁵, R⁶, R⁷ and R⁸ are, independently from each other, hydrogen atoms, hydroxyl groups, alkyl groups, cycloalkyl groups, alkoxy groups, aralkyl groups, aralkoxy groups, amino groups, substituted amino groups, cyano groups, nitro groups, substituted or unsubstituted aryl groups, substituted or unsubstituted heteroaryl groups, halogen atoms, halogenoalkyl groups or halogenoalkoxy groups, and two groups out of $R^5$ to $R^8$ may be combined together to form a ring, and W is a group represented by,

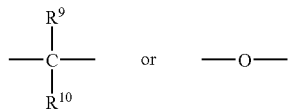

wherein $R^9$ and $R^{10}$ are, independently from each other, hydrogen atoms, hydroxyl groups, alkyl groups, cycloalkyl groups, alkoxy groups, aralkyl groups, aralkoxy groups, amino groups, substituted amino groups, cyano groups, nitro groups, substituted or unsubstituted aryl groups, substituted or unsubstituted heteroaryl groups, halogen atoms, halogenoalkyl groups or halogenoalkoxy groups.

2. A chromene compound according to claim 1, wherein the the divalent bridge group A is represented by the formula (1c-1).

3. A chromene compound according to claim 2, wherein, the ring Z is an alicyclic hydrocarbon ring which is a monocyclic ring having 3 to 20 carbon atoms or a crosslinking ring having 6 to 20 carbon atoms, or a heterocyclic ring which has at least one kind of group selected from the group consisting of imino group (—NR'—; R' is a hydrogen atom, an alkyl group or an aryl group), oxy group (—O—), thio group (—S—), carbonyl group (—CO—), carbonyloxy group (—COO—) and amide group (—NHCO—) as substitute for one or more methylene groups in the monocyclic ring or the crosslinking ring or has at least one nitrilo group as substitute for one or more methylidene groups in the crosslinking ring.

4. A chromene compound according to claim 2, wherein, in the ring Z, the alicyclic hydrocarbon ring or the heterocyclic ring have, as substituents, hydroxyl groups, alkyl groups, cycloalkyl groups, alkoxy groups, aralkyl groups, aralkoxy groups, amino groups, substituted amino groups, cyano groups, nitro groups, substituted or unsubstituted aryl groups, substituted or unsubstituted heteroaryl groups, halogen atoms, halogenoalkyl groups, halogenoalkoxy groups, or substituted or unsubstituted heterocyclic groups having a nitrogen atom as a hetero atom and bonded through the nitrogen atom.

5. A chromene compound according to claim 2, wherein, in the ring Z the heterocyclic ring is condensed with an aromatic hydrocarbon ring or with an aromatic heterocyclic ring.

6. A chromene compound according to claim 1, wherein the divalent bridge group A is represented by the formula (1c-2).

7. A chromene compound according to claim 6, wherein, in the formula (1c-2), $R^5$, $R^6$, $R^7$ and $R^8$ are, independently from each other, hydrogen atoms or alkyl groups having 1 to 4 carbon atoms, or two out of $R^5$ to $R^8$ are combined together to form a ring, and W is a group represented by,

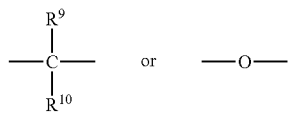

wherein $R^9$ and $R^{10}$ are, independently from each other, hydrogen atoms or alkyl groups having 1 to 4 carbon atoms.

8. A chromene compound according to claim 1, wherein, in the
in the ring X and the ring Y the aromatic hydrocarbon ring is one benzene ring or a condensed ring which is condensed with 2 to 4 benzene rings, or the aromatic heterocyclic ring is a 5-membered ring, 6-membered ring including oxygen, sulfur or nitrogen atom, or a condensed heterocyclic ring in which the above heterocyclic ring is condensed with a benzene ring or a heterocyclic ring, or a condensed heterocyclic ring in which the benzene ring is condensed with a heterocyclic ring.

9. A chromene compound according to claim 1 wherein, in the ring X or the ring Y, the aromatic hydrocarbon or the aromatic heterocyclic ring have, as substituents, hydroxyl groups, alkyl groups, cycloalkyl groups, alkoxy groups, aralkyl groups, aralkoxy groups, amino groups, substituted amino groups, cyano groups, nitro groups, substituted or unsubstituted aryl groups, substituted or unsubstituted heteroaryl groups, halogen atoms, halogenoalkyl groups, halogenoalkoxy groups, or substituted or unsubstituted heterocyclic groups having a nitrogen atom as a hetero atom and bonded through the nitrogen atom.

10. A chromene compound according to claim 1, wherein, in the ring X or the ring Y, the aromatic heterocyclic ring is a condensed heterocyclic ring in which a heterocyclic ring is condensed with an aromatic hydrocarbon ring or with an aromatic heterocyclic ring.

11. A chromene compound according to claim 1, wherein R' and $R^2$ in the general formula (1) are alkyl groups having 1 to 4 carbon atoms, aryl groups having 6 to 14 carbon atoms, or heteroaryl groups including oxygen, sulfur or nitrogen atom as a hetero atom and having a ring with 4 to 12 atoms.

12. A chromene compound according to claim 1, wherein the aryl group or heteroaryl group represented by $R^1$ and $R^2$ in the above general formula (1) have, as substituents, hydroxyl groups, alkyl groups, cycloalkyl groups, alkoxy groups, aralkyl groups, aralkoxy groups, amino groups, substituted amino groups, cyano groups, nitro groups, substituted or unsubstituted aryl groups, halogen atoms, halogenoalkyl groups, halogenoalkoxy groups, or substituted or unsubstituted heterocyclic groups having a nitrogen atom as a hetero atom and coupled through the nitrogen atom.

13. A chromene compound according to claim 1, wherein at least either $R^1$ or $R^2$ in the general formula (1) is:
(i) a substituted aryl group having a substituted amino group or an alkoxy group as a substituent;
(ii) a substituted aryl group having, as a substituent, a substituted or unsubstituted heterocyclic group that has a nitrogen atom as a hetero atom and is bonded through the nitrogen atom; or
(iii) a substituted aryl group having, as a substituent, a condensed heterocyclic ring in which the substituted or unsubstituted heterocyclic ring having the nitrogen atom as a hetero atom in (ii) above is condensed with an aromatic hydrocarbon ring or with an aromatic heterocyclic ring.

14. A photochromic material comprising a chromene compound of claim 1.

15. A photochromic optical material containing a chromene compound of claim 1.

* * * * *